United States Patent [19]

Tajima et al.

[11] Patent Number: 5,480,864
[45] Date of Patent: Jan. 2, 1996

[54] MODIFIED MAXADILAN PROTEIN, ITS PREPARATION AND USE, AND DNA ENCODING THE PROTEIN

[75] Inventors: Masahiro Tajima, Yokohama; Manami Ohnuma, Kanagawa, both of Japan; Ethan L. Lerner, Brookline, Mass.

[73] Assignees: Shiseido Co., Ltd., Japan; The General Hospital, Mass.

[21] Appl. No.: 102,757

[22] Filed: Aug. 6, 1993

[51] Int. Cl.$^6$ ............ A61K 38/00; C12P 21/06; C12N 9/48; C07H 19/00
[52] U.S. Cl. ............ 514/2; 435/69.1; 435/69.7; 435/214; 435/217; 514/12; 530/300; 530/324; 536/22.1; 536/23.1; 536/23.2; 536/23.4; 536/23.5; 536/24.1
[58] Field of Search ............ 435/69.1, 69.7, 435/214, 217; 530/300, 324; 514/2, 12; 536/22.1, 23.1, 23.2, 23.4, 23.5, 24.1

[56] References Cited

FOREIGN PATENT DOCUMENTS 0293249  11/1988  European Pat. Off. .
WOA-91/
00293  1/1991  WIPO .

OTHER PUBLICATIONS

International Search Report PCT/US94/08809 Lerner et al., Ethan A., "Maxadilan Cloning and Functional Expression of the Gene Encoding This Potent Vasodilator Peptide," J. Bio. Chem., vol. 267, No. 2, pp. 1062–1066 (1992).
Mandel, M., et al., Calcium–dependent Bacteriophage DNA Infection, J. Mol. Biol., 53:159–162 (1970).
Lerner, E., et al., Maxadilan—Cloning and Functional Expression of the Gene Encoding This Potent Vasodilator Peptide, Journal of Biological Chemistry, vol. 267, No. 2, Issue of Jan. 15, 1992, pp. 1062–1066.
Smith D., et al., Single–step Purification of Polypeptides Expressed in *Escherichia coli* as Fusions with Glutathione S–transferase, Gene, vol. 67, No. 1, Issue of Jul. 15, 1988, pp. 31–40.
Ribeiro et al., A Novel Vasodilatory Peptide from the Salivary Glands of the Sand Fly Lutzomyia longipalpis, Science, vol. 243, pp. 212–214 (1989).
Chang, Thrombin specificity—Requirement for Apolar Amino Acids Adjacent to the Thrombin Cleavage Site of Polypeptide Substrate, Eur. J. Biochem., vol. 151, pp. 217–224 (1985).

*Primary Examiner*—Robert A. Wax
*Assistant Examiner*—Hyosuk Kim
*Attorney, Agent, or Firm*—Finnegan, Henderson, Farabow, Garrett & Dunner

[57] ABSTRACT

A modified maxadilan protein exhibits higher biological activity than native maxadilan from the sand fly *Lutzomyia longipalpis*. A modified maxadilan fusion protein contains a thrombin cleavage site. This enables the production of the modified maxadilan as a fusion protein and recovery of the modified maxadilan after digestion with thrombin. The modified maxadilan is a potent vasodilator.

13 Claims, 7 Drawing Sheets pUC19-Max(60K,61A)-GK pUC19 BamHI site

GGATCCTGCTGTGTGATGCAACATGCCAATTTCGCAAGGCCATAGATGACTGCCAGAAGCAG
   I  L  C  D  A  T  C  Q  F  R  K  A₁₁I  D  D  C  Q  K  Q

GCGCATCATAGCAATGTTTTGCAGACTTCTGTACAAAACAACTGCCAACATTCACATCAATGGATACCTCC
 A  H  H₂₁S  N  V  L  Q  T  S  V  Q  T₃₁T  A  T  F  T  S  M  D  T  S

CAACTACCTGGAAATAGTGTCTTCAAAGAATGTATGAAGCAGAAGAAAAAGAATTTAAGGCAGGAAAGTGAATTC
 ₄₁Q  L  P  G  N  S  V  F  K  E₅₁C  M  K  Q  K  K  K  E  F  K₆₁A  G  K  * pUC 19
EcoRI site

FIG.1

```
  1  ATGTCCCCTATACTAGGTTATTGGAAAATTAAGGGCCTTGTGCAACCCACTCGACTTCTT   80
     M  S  P  I  L  G  Y  W  K  I  K  G  L  V  Q  P  T  R  L  L

61  TTGGAATATCTTGAAGAAAAATATGAAGAGCATTTGTATGAGCGCGATGAAGGTGATAAA  120
     L  E  Y  L  E  E  K  Y  E  E  H  L  Y  E  R  D  E  G  D  K

121  TGGCTAAACAAAAAGTTTGAATTGGGTTTGGAGTTTCCCAATCTTCCTTATTATATTGAT  180
     W  L  N  K  K  F  E  L  G  L  E  F  P  N  L  P  Y  Y  I  D

181  GGTGATGTTAAATTAACACAGTCTATGGCCATCATAGGTTATATAGCTGACAAGCACAAC  240
     G  D  V  K  L  T  Q  S  M  A  I  I  R  Y  I  A  D  K  H  N

241  ATGTTGGGTGGTTGTCCAAAAGAGCGTGCAGAGATTTCAATGCTTGAAGGAGCGGTTTTG  300
     M  L  G  G  C  P  K  E  R  A  E  I  S  M  L  E  G  A  V  L

301  GATATTAGATACGGTGTTTCGAGAATTGCATATAGTAAAGACTTTGAAACTCTCAAAGTT  360
     D  I  R  Y  G  V  S  R  I  A  Y  S  K  D  F  E  T  L  K  V

361  GATTTTCTTAGCAACCTACCTCAAATGCTGAAAATGTTCGAAGATCGTTTATGTCATAAA  420
     D  F  L  S  K  L  P  R  M  L  K  M  F  E  D  R  L  C  H  K

421  ACATATTTAAATGGTGATCATGTAACCCATCCTGACTTCATGTTGTATGACGCTCTTGAT  480
     T  Y  L  N  G  D  H  V  T  H  P  D  F  M  L  Y  D  A  L  D

481  GTTGTTTTATACATGGACCCAATGTGCCTGGATGCGTTCCCAAAATTAGTTTGTTTTAAA  540
     V  V  L  Y  M  D  P  M  C  L  D  A  F  P  K  L  V  C  F  K

541  AAACGTATTGAAGCTATCCCACAAATTGATAAGTACTTGAAATCCAGCAAGTATATACCA  600
     K  R  I  E  A  I  P  Q  I  D  K  Y  L  K  S  S  K  Y  I  A

601  TGGCCTTTGCAGGGCTGGCAAGCCACGTTTGGTGGTGGCGACCATCCTCCAAAATCGGAT  660
     W  P  L  Q  G  W  Q  A  T  F  G  G  G  D  H  P  P  K  S  D

661  CTGGTTCCGCGCGGATCGATCCTGTGTGATGCAACATGCCAATTTCGCAAGGCCATAGAT  720
     L  V  P  K  G  S  I  L  C  D  A  T  C  Q  F  R  K  A  I  D

721  GACTGCCAGAAGCAGGCGCATCATAGCAATGTTTTGCAGACTTCTGTACAAACAACTGCA  780
     D  C  Q  K  Q  A  H  H  S  N  V  L  Q  T  S  V  Q  T  T  A

781  ACATTCACATCAATGGATACCTCCCAACTACCTGGAAATAGTGTCTTCAAAGAATGTATG  840
     T  F  T  S  M  D  T  S  Q  L  P  G  N  S  V  F  K  E  C  M

841  AAGCAGAAGAAAAAGGAATTTAAGGCAGGAAAGTGAATTCATCCTGACTGACTCACG      897
     K  Q  K  K  K  E  F  K  A  G  K  *
```

FIG. 3

```
  1 ATGTCCCCTATACTAGGTTATTGGAAAATTAAGGGCCTTGTGCAACCCACTCGACTTCTT   60
    M  S  P  I  L  G  Y  W  K  I  K  G  L  V  Q  P  T  R  L  L

61 TTGGAATATCTTGAAGAAAAATATGAAGAGCATTTGTATGAGCGCGATGAAGGTGATAAA  120
    L  E  Y  L  E  E  K  Y  E  E  H  L  Y  E  R  D  E  G  D  K

121 TGGCTAAACAAAAAGTTTGAATTGGGTTTGGAGTTTCCCAATCTTCCTTATTATATTGAT  180
    W  L  N  K  K  F  E  L  G  L  E  F  P  N  L  P  Y  Y  I  D

181 GGTGATGTTAAATTAACACAGTCTATGGCCATCATACGTTATATAGCTGACAAGCACAAC  240
    G  D  V  K  L  T  Q  S  M  A  I  I  R  Y  I  A  D  K  H  N

241 ATGTTGGGTGGTTGTCCAAAAGAGCGTGCAGAGATTTCAATGCTTGAAGGACCCCTTTTC  300
    M  L  G  G  C  P  K  E  R  A  E  I  S  M  L  E  G  A  V  L

301 GATATTAGATACGGTGTTTCGAGAATTGCATATAGTAAAGACTTTGAAACTCTCAAAGTT  360
    D  I  R  Y  G  V  S  R  I  A  Y  S  K  D  F  E  T  L  K  V

361 GATTTTCTTAGCAAGCTACCTGAAATGCTGAAAATGTTCGAAGATCGTTTATGTCATAAA  420
    D  F  L  S  K  L  P  E  M  L  K  M  F  E  D  R  L  C  H  K

421 ACATATTTAAATGGTGATCATGTAACCCATCCTGACTTCATGTTGTATGACGCTCTTGAT  480
    T  Y  L  N  G  D  H  V  T  H  P  D  F  M  L  Y  D  A  L  D

481 GTTGTTTTATACATGGACCCAATGTGCCTGGATGCGTTCCCAAAATTAGTTTGTTTTAAA  540
    V  V  L  Y  M  D  P  M  C  L  D  A  F  P  K  L  V  C  F  K

541 AAACGTATTGAAGCTATCCCACAAATTGATAAGTACTTGAAATCCAGCAAGTATATAGCA  600
    K  R  I  E  A  I  P  Q  I  D  K  Y  L  K  S  S  K  Y  I  A

601 TGGCCTTTGCAGGGCTGGCAAGCCACGTTTGGTGGTGGCGACCATCCTCCAAAATCGGAT  660
    W  P  L  Q  G  W  Q  A  T  F  G  G  G  D  H  P  P  K  S  D

661 CTGATCGAAGGTCGTGGGATCCTGTGTGATGCAACATGCCAATTTCGCAAGGCCATAGAT  720
    L  I  E  G  R  G  I  L  C  D  A  T  C  Q  F  R  K  A  I  D

721 GACTGCCAGAAGCAGGCGCATCATAGCAATGTTTTGCAGACTTCTGTACAAACAACTGCA  780
    D  C  Q  K  Q  A  H  H  S  N  V  L  Q  T  S  V  Q  T  T  A

781 ACATTCACATCAATGGATACCTCCCAACTACCTGGAAATAGTGTCTTCAAAGAATGTATG  840
    T  F  T  S  M  D  T  S  Q  L  P  G  N  S  V  F  K  E  C  M

841 AAGCAGAAGAAAAAGGAATTTAAGGCAGGAAAGTGAATTCATCGTGACTGACTGACG     897
    K  Q  K  K  K  E  F  K  A  G  K  *
```

FIG. 4

GSIL-60K,61A-MAX-GK

```
GGATCGATCCTGCTGTGTGATGCAAGCCAATTTCGCAAGGCCATAGATGACTGCCAGAAGCAG
 G  S  I  L  C  D  A  T  C  Q  F  R  K  A₁₁ D  D  C  Q  K  Q

GCGCATCATAGCAATGTTTTGCAGACTTCTGTACAAACAACTGCAACATTCACATCAATGGATACCTCC
 A  H  H₂₁ S  N  V  L  Q  T  S  V  Q  T₃₁ T  A  T  F  T  S  M  D  T  S

CAACTACCCTGGAAATAGTGTCTTCAAAGAATGTATGAAGCAGAAGAAAAAGGAATTTAAGGCAGGAAAGTAA
₄₁Q  L  P  G  N  S  V  F  K  E₅₁ C  M  K  Q  K  K  K  E  F  K₆₁ A  G  K  *
```

MODIFIED MAXADILAN PROTEIN, ITS PREPARATION AND USE, AND DNA ENCODING THE PROTEIN

BACKGROUND OF THE INVENTION

A. Field of the Invention

The present invention relates to a modified maxadilan protein, a potent vasodilator peptide, and to a modified maxadilan fusion protein. This invention also relates to DNA sequences encoding modified maxadilan and modified maxadilan fusion proteins and vectors comprising these DNA sequences. The present invention further relates to a method of producing modified maxadilan having increased specific activity and to a method for increasing the yield of maxadilan protein produced using recombinant methods.

B. Description of the Prior Art

Maxadilan is a potent vasodilator peptide, which is present in the saliva of the sand fly *Lutzomyia longipalpis*. This sand fly spreads the disease leishmaniasis by secreting the protozoan parasite, Leishmania, into its victim when the sand fly probes for a blood meal. It is believed that the potent vasodilating effects of maxadilan enhance the infectivity of the parasite. Maxadilan is useful as a therapeutic agent, which can increase blood flow to defined areas in a patient's body.

In order to fully characterize the biological activity of maxadilan and to thoroughly investigate the therapeutic uses for this important protein, an adequate supply of maxadilan protein is essential. At present, maxadilan can be obtained by purification of salivary maxadilan from sand fly salivary glands or by recombinant DNA methods. Lerner et al. and Shoemaker have cloned and expressed the gene for maxadilan as a fusion protein with glutathione S-transferase (GST), a bacterial protein. Lerner et al., "Maxadilan: Cloning And Functional Expression Of A Gene Encoding This Potent Vasodilator Peptide," *Journal of Biological Chemistry*, Vol. 267, No. 2, pp. 1062–66, 1992.

The GST fusion protein is cleaved by Factor Xa to release maxadilan protein. Factor Xa is an expensive cleavage enzyme and does not cleave the maxadilan GST fusion protein as efficiently as desired. Because of the high cost and lower than desired cleavage efficiency of Factor Xa, there exists a need in the art for large quantities of recombinant maxadilan that can be produced less expensively and more efficiently.

SUMMARY OF THE INVENTION

Accordingly, this invention aids in fulfilling these needs in the art by providing a modified maxadilan protein, wherein the peptide G-S-I-L is SEQ ID NO: 1 fused to the N-terminus of native maxadilan protein. In one embodiment of the invention, the modified maxadilan protein has the residue G-S-I-L-C-D-A-T SEQ ID NO: 2 as the first eight amino acids at the N-terminus of the protein.

This invention also provides a DNA sequence encoding a modified maxadilan protein of the invention. The DNA sequence is useful for producing the modified maxadilan protein.

In addition, this invention provides a vector containing the DNA sequence of the invention. The vector can be one that is suitable for replication or expression in a prokaryotic or eucaryotic host. A host cell microorganism comprising the vector of the invention is also provided.

2

Further, this invention provides a fusion protein comprising a bacterial protein fused at its C-terminus to the N-terminus of the peptide L-V-P-R-G-S-I-L SEQ ID NO: 3, and further comprising maxadilan native protein fused at its N-terminus to the C-terminus of said peptide. The bacterial protein is glutathione S-transferase in a typical fusion protein of the invention.

Moreover, this invention provides a method of producing a fusion protein of the invention by culturing host cells of the invention under suitable growth conditions so that recombinant modified maxadilan fusion protein is produced.

In another method of producing a modified maxadilan protein of the invention, host cells of the invention are cultured under suitable growth conditions so that recombinant maxadilan fusion protein is produced, and the recombinant fusion protein is cleaved with thrombin to yield modified maxadilan. The modified maxadilan proteins produced by the methods of the invention are also provided.

This invention further provides a vasodilation composition comprising, as an effective component, a modified maxadilan protein of the invention. The modified maxadilan exhibits vasodilation activity in mammals. The composition of this invention provides excellent effects by topical application and subcutaneous injection.

Moreover, this invention provides a method for inducing, maintaining or increasing vasodilation in a mammal. The method comprises administering a vasodilation inducing, maintaining, or increasing amount of modified maxadilan protein of the invention.

This invention also provides a composition suitable for topical application to mammalian skin. The composition comprises modified maxadilan protein in a vasodilation inducing, maintaining or increasing amount in a pharmaceutically acceptable vehicle.

It has been discovered that the modified maxadilan of the invention has a specific activity that is at least 10 times that of native maxadilan or maxadilan cleaved from the GST fusion protein heretofore employed. It has been further discovered that the process of producing recombinant modified maxadilan, comprising cleavage of the fusion protein with thrombin, more than doubles the amount of modified maxadilan than was produced using Factor Xa to cleave the GST fusion protein.

BRIEF DESCRIPTION OF THE DRAWINGS

The accompanying drawings, which are incorporated in and constitute a part of this specification, illustrate several embodiments of the invention and together with the description, serve to explain the principles of the invention. In the drawings:

FIG. 1 depicts the cDNA sequence of the BamHI/EcoRI a fragment from plasmid pUC19-Mas (60K, 61A)-GK SEQ ID NO: 4 and SEQ ID NO. 5;

FIG. 3 depicts an amino acid and DNA sequence of a GST-modified maxadilan fusion protein of the invention (SEQ ID NO: 8 and SEQ ID NO: 9);

FIG. 4 is the amino acid and DNA sequence of a GST-GIL maxadilan fusion protein (SEQ ID NO: 10 and SEQ ID NO: 11);

FIG. 7 depicts an amino acid and DNA sequence of a modified maxadilan protein of the invention (SEQ ID NO: 12 and SEQ ID NO: 13); and

DESCRIPTION OF THE PREFERRED EMBODIMENT

Figure 2:
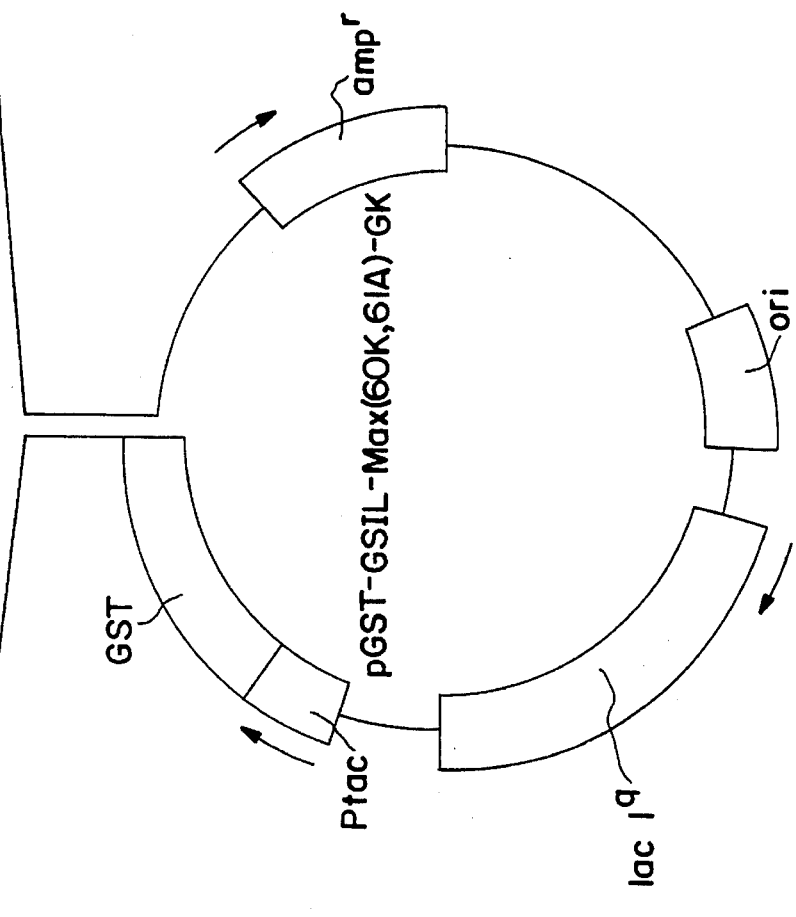
FIG. 2 depicts the structure of plasmid pGST-GSIL-Max (60K, 61A)-GK (SEQ ID NO: 3, SEQ ID NO: 6, and SEQ ID NO: 7)

The present invention relates to modified maxadilan proteins having the N-terminal sequence G-S-I-L-C-D-A-T SEQ ID NO: 2 and processes for producing those proteins. The process of the invention allows production of modified maxadilan at levels more than double the level produced by prior art methods. The modified maxadilan proteins of the invention have high biological activity. The biological activity using a skin erythema assay is at least 10 times the activity of native maxadilan or of maxadilan cleaved from the recombinant maxadilan fusion protein heretofore employed.

1. Definitions

In order that the invention can be more fully understood, following are definitions of terms employed herein.

a. Amino Acid Definitions

The following standard abbreviations and symbols are used herein to identify amino acid residues.

| Amino Acid | Three-Letter Abbreviation | One-Letter Symbol |
|---|---|---|
| Alanine | Ala | A |
| Arginine | Arg | R |
| Asparagine | Asn | N |
| Aspartic acid | Asp | D |
| Asparagine or aspartic acid | Asx | B |
| Cysteine | Cys | C |
| Glutamine | Gln | Q |
| Glutamic acid | Glu | E |
| Glutamine or glutamic acid | Glx | Z |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V | b. G-S-I-L Peptide

A peptide having the sequence Glycine-Serine-Isoleucine-Leucine is identified herein as "G-S-I-L" SEQ ID NO: 1 peptide. The N-terminus of the amino acid sequence is the first amino acid, going from left to right. The last amino acid is the C-terminus. Thus, G-S-I-L peptide has the amino acid residue glycine (G) as its N-terminus and the amino acid residue leucine (L) as its C-terminus.

c. G-I-L Peptide

A peptide having the sequence Glycine-Isoleucine-Leucine is identified herein as "G-I-L" peptide. Using the same convention, G-I-L peptide has a glycine residue (G) as its N-terminus and the amino acid residue leucine (L) as its C-terminus.

d. Native Maxadilan Protein

The term "native maxadilan protein" is used herein to identify maxadilan protein, which the sand fly *Lutzomyia longipalpis* can produce, wherein the protein exhibits vasodilation activity in a mammal. The terms "native maxadilan protein" and "native maxadilan" are used interchangeably herein.

e. Modified Maxadilan Protein

"Modified maxadilan protein" is a protein comprising native maxadilan protein having an N-terminus, wherein the first four amino acids of the N-terminus are G-S-I-L SEQ ID NO: 1. The terms "modified maxadilan protein," "modified maxadilan," and "G-S-I-L SEQ ID NO: 1 maxadilan" are used interchangeably herein.

f. Modified Maxadilan Fusion Protein

"Modified maxadilan fusion protein" is a modified maxadilan protein to which additional amino acids have been added.

g. G-I-L Maxadilan

A native maxadilan protein having the N-terminus of G-I-L is referred to herein as "G-I-L maxadilan".

h. Nucleotide Definitions

The following standard abbreviations are used to identify nucleotides by the chemical names of their bases:

| | |
|---|---|
| Adenine | A |
| Thymine | T |
| Guanine | G |
| Cytosine | C |
| Uracil | U |

2. Native Maxadilan Proteins

Peptides from salivary gland lysates of the sand fly were previously identified and shown to be capable of vasodilation and of temporary immune suppression in mammals. See, International Patent Publication No. WO91/00293 of Lerner et al.; and Ribeiro et al., *Science*, Vol. 243, pp. 212–214 (1989). The term Lutzomyia protein as used herein refers to all such peptides, active analogs, and active fragments. Maxadilan or active fragments thereof are examples of suitable Lutzomyia proteins for use in the present invention. Maxadilan has a molecular weight of about 6800 daltons and will be used as a representative peptide in the following description of the invention.

At least two variants of Lutzomyia protein have been reported in the literature. The nucleotide sequence of the cDNA and the deduced amino acid sequence of one form of mature Lutzomyia protein are as follows:

| TGT | GAT | GCA | ACA | TGC | CAA | TTT | CGC | AAG | KCC | ATA | GAT | GAC | TGC | |
|---|---|---|---|---|---|---|---|---|---|---|---|---|---|---|
| Cys | Asp | Ala | Thr | Cys | Gln | Phe | Arg | Lys | Ala | Ile | Asp | Asp | Cys | 42 |
| CAG | AAG | CAG | GCG | CAT | CAT | AGC | AAT | GTT | TTG | CAG | ACT | TCT | GTA | CAA |
| | | | | | | | | | | | | | | 87 |

| | | | | | | | | | | | | | |
|---|---|---|---|---|---|---|---|---|---|---|---|---|---|
| Gln | Lys | Gln | Ala | His | His | Ser | Asn | Val | Leu | Gln | Thr | Ser | Val | Gln |
| ACA | ACT | GCA | ACA | TTC | ACA | TCA | ATG | GAT | ACC | TCC | CAA | CTA | CCT | GGA |
| Thr | Thr | Ala | Thr | Phe | Thr | Ser | Met | Asp | Thr | Ser | Gln | Leu | Pro | Gly | 132 |
| AAT | AGT | GTC | TTC | AAA | GAA | TGT | ATG | AAG | CAG | AAG | AAA | AAG | GAA | TTT |
| Asn | Ser | Val | Phe | Lys | Glu | Cys | Met | Lys | Gln | Lys | Lys | Lys | Glu | Phe | 177 |
| AAG | GCA | GGA | AAG | TAA | AAT | GAT | TGA | AGA | AAA | TTG | TAG | CCG | AGG | AGA |
| Lys | Ala | Gly | Lys | SEQ ID NO: 15 | | | | | | | | | | 222 |
| GAAAGAAAGA | | AAGTCCCATA | | CCATATTTTG | | TTTGTTAATT | | GTAACGAATTC | | | | | | 272 |
| TTCCGAAAAA | | ATAAATATT | | ATGCACTCAA | | TTTAAAAAAA | | A SEQ ID NO: 14 | | | | | | 313 |

The genomic Lutzomyia protein DNA sequence and the deduced amino acid sequence are as follows:

reported in Lerner et al. at page 1064.

| ATG | AAA | TAT | TCT | TTA | AAT | AAT | CTC | CAT | TTT | CTT | GTA | GAC | GTT | GCT | |
|---|---|---|---|---|---|---|---|---|---|---|---|---|---|---|---|
| Met | Lys | Tyr | Ser | Leu | Asn | Asn | Leu | His | Phe | Leu | Val | Asp | Val | Ala | 45 |
| GAG | GGC | TGT | GAT | GCA | ACA | TGT | CAA | TTT | CGC | AAG | GCC | ATA | GAA | GAC | |
| Glu | Gly | Cys | Asp | Ala | Thr | Cys | Gln | Phe | Arg | Lys | Ala | Ile | Glu | Asp | 90 |
| TGC | AGG | AAG | AAG | GCG | CAT | CAT | AGC | GAT | GTT | TTG | CAG | ACT | TCT | GTA | |
| Cys | Arg | Lys | Lys | Ala | His | His | Ser | Asp | Val | Leu | Gln | Thr | Ser | Val | 135 |
| CAA | ACA | ACT | GCA | ACA | TTT | ACA | TCA | ATG | GAT | ACC | TCC | CAA | CTA | CCT | |
| Gln | Thr | Thr | Ala | Thr | Phe | Thr | Ser | Met | Asp | Thr | Ser | Gln | Leu | Pro | 180 |
| GGA | AGT | GGT | GTT | TTC | AAA | GAA | TGC | ATG | AAG | GAG | AAA | GCT | AAG | GAA | |
| Gly | Ser | Gly | Val | Phe | Lys | Glu | Cys | Met | Lys | Glu | Lys | Ala | Lys | Glu | 225 |
| TTT | AAG | GCA | GGA | AAG | TAG | SEQ ID NO: 16 | | | | | | | | | |
| Phe | Lys | Ala | Gly | Lys | SEQ ID NO: 17 | | | | | | | | | | 243 |

The genomic native Lutzomyia protein DNA sequence varies somewhat from the native Lutzomyia protein cDNA sequence and is believed to represent a variant native maxadilan protein gene. The genomic Lutzomyia protein DNA sequence includes the DNA sequence and deduced amino acid sequence of a 17 amino acid leader peptide. The signal sequence of Lutzomyia protein is also given in the genomic DNA sequence (nucleotides 1–51).

Native maxadilan can be obtained by conventional purification chromatography from surgically excised salivary glands of *Lutzomyia longipalpis*. One pair of salivary glands contains about 10–15 ng native maxadilan. The native maxadilan constitutes about 1% of the total protein in the salivary glands of the sand fly *Lutzomyia longipalpis*.

Knowledge of the native maxadilan protein sequence enables the skilled artisan to produce large quantities of the protein for therapeutic use. The native maxadilan protein can also be synthesized using conventional chemical solid or solution phase peptide synthesis techniques.

The following is a nucleotide sequence and amino acid translation of the PCR-amplified cDNA fragment generated with the 3-13 primer (overlined) and the oligo (dT) primer (binding site underlined). A Y in the 3-13 primer sequence indicates both C and T at those positions. This sequence was

|  | 3-13 primer |  |  |  |  |  |  |  |  |  |  |  |  |  |
|---|---|---|---|---|---|---|---|---|---|---|---|---|---|---|
| GCYACCGAYCAGTTCCGYAAGGCYATYGAYGAC |  |  |  |  |  |  |  | TGC | CAG | AAG | CAG | GCG | CAT | 51 |
|  |  |  |  |  |  |  |  | Cys | Gln | Lys | Gln | Ala | His |  |
| CAT | AGC | AAT | GTT | TTG | CAG | ACT | TCT | GTA | CAA | ACA | ACT | GCA | ACA | TTC | 96 |
| His | Ser | Asn | Val | Leu | Gln | Thr | Ser | Val | Gln | Thr | Thr | Ala | Thr | Phe |  |
| ACA | TCA | ATG | GAT | ACC | TCC | CAA | CTA | CCT | GGA | AAT | AGT | GTC | TTC | AAA | 141 |
| Thr | Ser | Met | Asp | Thr | Ser | Gln | Leu | Pro | Gly | Asn | Ser | Val | Phe | Lys | SEQ ID NO: 19 |
| GAA | TGT | ATG | AAG | CAG | AAG | AAA | AAG | GAA | TTT | AGT | TCA | GGA | AAG | TAA | 186 |
| Glu | Cys | Met | Lys | Gln | Lys | Lys | Lys | Glu | Phe | Ser | Ser | Gly | Lys--- |  |  |
| AAGATTGAAG | AAAATTGTAG | CCGAGGAGAG | AAAGAAAGAA | AGTCCCATAC | 236 |
| CATATTTTGT | TTGTTAATTG | TAACGAATTT | TCCGAAAAAA | TAAAATATTA | 286 |
| TGCACTCAAT | TTA | AAAAAAAAAAAAAAAAAGGGGCCTCCC | SEQ ID NO: 18 | 325 |
|  |  | oligo dT primer |  |  |

The nucleotide sequence and translation of the PCR-amplified maxadilan gene fragment generated with an upstream primer (not shown) and the 3'-UT primer (binding site underlined) are as follows. The positions of the A, B, C, and D primers are overlined.

| AAT | CAA | TTG | CTA | AAA | AAA | AAT | TAC | AAA | TAG | AAC | TAC | TAC | AGA | TGT | 45 |
|---|---|---|---|---|---|---|---|---|---|---|---|---|---|---|---|
| TCT | GAA | TTT | TTT | CTT | GAT | ATT | CTT | TCT | CAA | TTG | GATG |  |  |  | 81 |
|  |  | A |  |  |  | *cap? |  | B |  |  |  |  |  |  | 139 |
| TATAAAAGAGGCTATTTTGTGCTGATTTTGTTAGTCAGTATTCTGATAAACTACAAAA |  |  |  |  |  |  |  |  |  |  |  |  |  |  |  |
|  |  |  |  | C |  |  |  |  |  |  |  |  |  |  |  |
| ATG | AAG | CAA | ATC | CTT | TTAATCTCTTTGGTGGTGGTT |  |  |  |  |  | CTT | GCC | GTG | TTT | 187 |
| Met | Lys | Gln | Ile | Leu | LeuIleSerLeuValValVal |  |  |  |  |  | Leu | Ala | Val | Phe |  |
| GCC | TTC | AGT | AAG | TTC | TTC | CTT | TAG | GCC | TTT | CCT | TCT | CAA | AAC | TTA | 232 |
| Ala | Phe | A |  |  |  |  |  |  |  | ...intron... |  |  |  |  |  |
| AAG | TAA | TTT | AAT | GAA | ATA | TTC | TTT | AAA | TAA | TCT | CCA | TTT | TCT | TGT | 277 |
|  |  |  |  |  |  | ... |  |  |  |  |  |  |  |  |  |
| AGACGTTGCT |  | GAG | GGC | TGT | GAT | GCA | ACA | TGC | CAA | TTT | CGC | AAG | GCC | 323 |
| ...snValAla |  | Glu | Gly | Cys | Asp | Ala | Thr | Cys | Gln | Phe | Arg | Lys | Ala |  |
| ATA | GAT | GAC | TGC | CAG | AAG | CAG | GCG | CAT | CAT | AGC | AAT | GTT | TTG | CAG | 368 |
| Ile | Asp | Asp | Cys | Gln | Lys | Gln | Ala | His | His | Ser | Asn | Val | Leu | Gln |  |
| ACT | TCT | GTA | CAA | ACA | ACT | GCA | ACA | TTC | ACA | TCA | ATG | GAT | ACC | TCC | 413 |
| Thr | Ser | Val | Gln | Thr | Thr | Ala | Thr | Phe | Thr | Ser | Met | Asp | Thr | Ser |  |
| CAA | CTA | CCT | GGA | AAT | AGT | GTC | TTC | AAA | GAA | TGT | ATG | AAG | CAG | AAG | 458 |
| Gln | Leu | Pro | Gly | Asn | Ser | Val | Phe | Lys | Glu | Cys | Met | Lys | Gln | Lys |  |
| AAA | AAG | GAA | TTT | AGT | TCA | GGA | AAG | TAA | AAG | ATT | GAA | GAA | AAT | TGT | 503 |
| Lys | SEQ ID NO: 21 |  | Glu | Phe | Ser | Ser | Gly | Lys--- |  |  |  |  |  |  |  |

| | | | | | | | | | | | | | | |
|---|---|---|---|---|---|---|---|---|---|---|---|---|---|---|
| AGC | CGA | GGA | GAG | AAA | GAA | AGA | AAG | TCC | CAT | ACC | ATA | TTT | TGT | TTG | 548
| TTA | ATT | <u>GTAACGAATTTTCCGAAA</u> | | | SEQ ID NO: 20 | | | | | | | | | 573 |
| | | 3'UT primer | | | | | | | | | | | | |

The COOH-terminal PCR primer used by Lerner et al. was designed based on a different sand fly isolate than the isolate used to generate the DNA libraries. Thus, the COOH terminus of recombinant maxadilan has Lys-Ala at positions 60–61 rather than the Ser-Ser encoded by the cDNA and gene sequences shown above. Lerner et al. at page 1063.

Instead of its primary amino acid structure, native maxadilan protein suitable for use in this invention can be characterized by its chemical and biological properties. Specifically, the native maxadilan protein suitable for use in this invention is capable of inducing vasodilation or temporary immune suppression in a mammal. The vasodilatory activity of the native maxadilan protein is shown by relaxation of at least about 100% of a constricted rabbit aortic ring as described in International Patent Publication No. WO91/00293. Temporary immune suppression is demonstrated by the assay of $H_2O_2$ production by macrophages as a marker of immune stimulation as described in International Patent Publication No. WO91/00293, such that $H_2O_2$ production is depressed by at least about 75% in the assay.

In one embodiment of the invention, the native maxadilan protein has a molecular weight of about 6839 daltons as determined by mass spectrometry. In another embodiment, the native maxadilan protein employed in this invention is characterized by reference to calcitonin gene-related peptide (CGRP). That is, the native maxadilan protein is characterized by elution prior to CGRP in an acetonitrile-$H_2O$-trifluoroacetic acid elution in a reverse-phase high performance liquid chromatography column. See, International Patent Publication No. WO91/00293. The native maxadilan protein can also be characterized as having vasodilation activity as measured by erythema induction in animal skin of at least about 80–100 times that of CGRP as measured by the assay described in International Patent Publication No. WO91/00293.

Native maxadilan protein or its active analogs and fragments can be used in carrying out this invention. The active analogs and fragments of native maxadilan protein are typically proteins comprising an amino acid sequence sufficiently duplicative of the sequence of the active portion of the native maxadilan protein such that the proteins are capable of inducing, maintaining or increasing the biological effects of native maxadilan in a mammal. The proteins of the present invention need not be identical to those disclosed in International Patent Publication No. WO 91/00293 or to those disclosed in this specification. Variations can be attributable to local mutations, which do not substantially detract from the biological properties associated with native maxadilan protein. Such variations can be found in proteins isolated from lysates as well as chemically or recombinantly constructed proteins.

3. The Modified Maxadilan Proteins Of The Invention

Native maxadilan protein has the N-terminal sequence C-D-A-T SEQ ID NO: 22. This invention provides modified maxadilan protein, which is native maxadilan protein having the N-terminal sequence G-S-I-L-C-D-A-T SEQ ID NO: 2.

The modified maxadilan protein of the invention has a higher biological activity than native maxadilan protein. More particularly, the biological activity of the modified maxadilan is at least 10 times the activity of native maxadilan in a skin erythema assay.

4. The Modified Maxadilan Fusion Proteins Of This Invention

In another embodiment of this invention, the modified maxadilan protein has an N-terminus, and proximate to the N-terminus of the protein there is engineered a cleavage site for the protease thrombin so that cleavage of a fusion protein will yield a polypeptide comprising modified maxadilan protein having vasodilator activity in a mammal. The thrombin cleavage site is engineered by providing upstream of the N-terminus of the modified maxadilan protein suitable amino acids for which thrombin is specific.

Thrombin is a protease that cleaves polypeptide substrates at Arg/Lys-Xaa bonds. These amino acid residues are fused to the modified maxadilan proximate to the N-terminus of the protein. For efficient cleavage by thrombin, Arg or Lys should be provided adjacent to the thrombin cleavage site of the modified maxadilan substrate. For example, suitable cleavage sites for thrombin have the structures of (a) P4-P3-Pro-Arg-P1'-P2', where P3 and P4 are hydrophobic amino acids and P1'and P2' are nonacidic amino acids; and (b) P2-Arg-P1', where P2 or P1' are Gly. See *Eur. J. Biochem.*, 151, 217–224 (1985). In the preferred embodiment of this invention, the cleavage site for thrombin has the structure P2-Arg-P1', wherein P2 is Val and P1' is Gly, and P1' coincides with the N-terminus of the modified maxadilan protein.

The thrombin cleavage site is provided within four amino acids upstream of the N-terminus of the modified maxadilan protein. In the preferred embodiment of this invention, the amino acids comprising the thrombin cleavage site are fused directly to the N-terminus of modified maxadilan.

In a preferred embodiment of this invention, a modified maxadilan fusion protein comprises a modified maxadilan protein fused at its N-terminus to the C-terminus of the peptide L-V-P-R SEQ ID NO . It has surprisingly been found that alteration of native maxadilan by fusion of the peptide L-V-P-R-G-S-I-L to the N-terminus of native maxadilan provides a site where thrombin can cleave to yield modified maxadilan of the invention in high yield, high purity, and high biological activity.

The modified maxadilan fusion protein comprising modified maxadilan fused to a thrombin recognition sequence can be further fused at its N-terminus to the C-terminus of a heterologous polypeptide to facilitate production, processing, and recovery of the protein. In a preferred embodiment of this invention, a modified maxadilan fusion protein with glutathione S-transferase (GST) is provided with a thrombin recognition sequence between GST and the modified maxadilan protein. The use of GST in the fusion protein is advantageous because it facilitates purification by means of a glutathione-agarose affinity column prior to digestion with the thrombin. It will be understood that fusion proteins of modified maxadilan with other polypeptides can be employed in this invention. Examples of other fusion proteins are those based on β-galactosidase, thymidine kinase, chloroamphenicol acetyl transferase, protein A and secretable proteins.

5. Expression Of The Proteins Of This Invention

While the modified maxadilan protein of the invention can be synthesized by chemical techniques, preparation of modified maxadilan by recombinant techniques provides a good source of the protein with a higher level of purity and at lower cost than heretofore attainable. More particularly, modified maxadilan protein can be prepared by expression of a DNA sequence encoding the protein in a suitable microorganism. This invention thus includes a DNA sequence that encodes the modified maxadilan protein or fusion proteins of the invention.

DNA encoding native maxadilan protein can be prepared by conventional techniques. For example, RNA can be extracted from dissected salivary glands of the sand fly *Lutzomyia longipalpis*. The RNA can be reverse transcribed to form cDNA, and the cDNA can be amplified by polymerase chain reaction using appropriate primers. As the complete native maxadilan coding sequence is known, the native maxadilan gene can be amplified by PCR. This technique is described by Lerner et al., *J. Biol. Chem.*, 267:1062–1066 (1992). Substitution of codons preferred by the host cell utilized in the production of the proteins of the invention may further increase the yield of recombinant maxadilan.

The DNA encoding the native maxadilan protein is modified by ligation of a DNA fragment encoding G-S-I-L SEQ ID NO: 1 peptide or the peptide L-V-P-R-G-S-I-L SEQ ID NO: 3 if a thrombin recognition site is desired. The DNA fragment can be in single-stranded or double-stranded form. If the fragment is in single-stranded form, it can be converted to double-stranded form using DNA polymerase according to conventional techniques.

The nucleic acid fragment to be ligated to the DNA encoding native maxadilan protein can have cohesive ends compatible with any combination of sites. Alternatively, the nucleic acid fragment can have one or more blunt ends that can be ligated to corresponding blunt ends of the DNA encoding the protein. The nucleic acid fragment to be ligated can be further processed, if desired, by successive exonuclease digestion. In the event the nucleic acid fragment to be ligated does not contain a desired combination of cohesive ends, the fragment can be modified by adding a linker or an adaptor.

A wide variety of host cells and expression vectors can be employed in producing the modified maxadilan proteins of the invention. The selection of the appropriate host and expression vector is controlled by a number of variables that are well known in the art. These variables include, but are not limited to, the toxicity and ease of purification of the protein fused to maxadilan, ease of expression of the fusion protein, and cost.

In a preferred embodiment of this invention, modified maxadilan protein is prepared from a DNA sequence encoding native maxadilan, wherein the DNA sequence encoding the native maxadilan has a 5' end to which is linked a DNA sequence encoding the peptide L-V-P-R-G-S-I-L SEQ ID NO: 23. The maxadilan precursor polypeptide encoded by the resulting DNA sequence has a cleavage site for the enzyme thrombin. It has been unpredictably discovered that the cleavage site is accessible to the enzyme thrombin and that thrombin does not adversely affect the biological activity of the modified maxadilan protein. Cleavage of this precursor polypeptide with thrombin yields modified maxadilan protein without the use of Factor Xa. Moreover, it has been unexpectedly discovered that thrombin cleaves more efficiently than Factor Xa cleaves the maxadilan precursor polypeptide used heretofore.

In another preferred embodiment of this invention, the modified maxadilan protein is prepared by expression of a DNA sequence encoding native maxadilan protein, wherein the native maxadilan protein has a 5' end to which is linked a first DNA sequence encoding the peptide L-V-P-R-G-S-I-L SEQ ID NO: 3 and a second DNA sequence linked to the first DNA sequence upstream of the first DNA sequence. The second DNA sequence encodes the heterologous peptide previously described. An example of a heterologous peptide is glutathione S-transferase. The DNA sequence for this peptide is well-known in the art. See Smith et al., *Gene* (Amst.) 67:31–40 (1988).

The bacterial subcloning vectors M13 mp10 and M13 mp11 were used for subcloning cDNA in the present invention. Other suitable subcloning vectors include pUC18 and pUC19. The present invention has been carried out using a bacterial fusion protein, bacterial expression vectors, and bacterial host cells. Other expression systems can be employed to express modified maxadilan fusion proteins that can be cleaved by thrombin. For example, yeast and mammalian expression vectors can be employed. Typical vectors are pMC1871, pEZZ18, pMSG-CAT, pCH110, and pBPV. The preferred expression vector of the invention is pGEX-2T because it contains a DNA sequence encoding a thrombin cleavage site.

Many different cells are suitable for producing the proteins of the instant invention. These include well-known host cells, such as bacteria (*B. subtilus, E. coli*), yeast cells and mammalian cells. The preferred host cells for expression of the proteins of this invention include *E coli* containing lac $I^q$ for example, *E. coli* JM105 and M15.

As previously noted, cleavage of the modified maxadilan fusion protein of the invention with thrombin provides modified maxadilan. Thrombin concentrations of about 1 μg/ml to about 100 mg/ml can be employed to cleave about 1 μg/ml to about 10 g/ml of the modified maxadilan fusion protein. Thrombin digestion can be carried out for about 5 minutes to about 30 hours at temperatures of about 15° C. to about 40° C. at a pH of about 6 to about 9 and in the presence of a buffer Examples of suitable buffers are HEPES-HCl, TRIS-HCl, sodium phosphate or potassium acetate buffer. The preferred buffer is TRIS-HCl. Cleavage of the fusion proteins of the invention with 10 μg/ml thrombin for 1 hour at 37° C. and a pH of 7.4 in the presence of 50 mM TRIS-HCl as buffer has been found to produce modified maxadilan protein having high purity and high biological activity following purification by reverse phase HPLC.

The proteins of the invention are recovered from the cleavage digest and then purified. Preferably, the proteins are purified by reverse phase high pressure liquid chromatography (RP-HPLC), although other purification methods known in the art can be employed. Typical of these other purification methods are ion exchange chromatography and gel filtration.

An example of expression of the native maxadilan protein by recombinant techniques can be found in the article entitled "Expression of Recombinant Maxadilan, Maxadilan, Cloning and Functional Expression of the Gene Encoding This Potent Vasodilator Peptide," *Journal of Biological Chemistry*, Vol. 267, No. 2, Issue of January 15, pp. 1063, Ethan Lerner and Charles Shoemaker, authors.

6. Compositions And Methods Of Using The Modified Maxadilan Protein Of This Invention The modified maxadilan protein of the invention is useful for inducing, maintaining or increasing vasodilation in mammals by administering an effective amount of the protein to the mammal. It is preferable that the subject is a human, although the compositions and methods of the invention can be employed with other primates and other animals, such as sheep, rabbits, mice, rats and other mammalia. The protein can be applied to the desired site by topical application or by subcutaneous injection.

(a) Composition for Topical Application

The composition of the invention can be formulated into a form suitable for topical application by incorporating the modified maxadilan protein in a suitable vehicle. The vehicle for topical application is a substance that acts as a diluent, dispersant, or solvent for the modified maxadilan protein and other reagents in the composition so that the composition can be applied to and distributed substantially evenly over the skin at an appropriate concentration. The vehicle is preferably one that aids penetration of the modified maxadilan protein into the skin to reach the immediate environment where vasodilation is desired.

The vehicle can be a solid, semi-solid or liquid vehicle that is cosmetically acceptable, pharmaceutically acceptable, or physiologically acceptable, and which enables the modified maxadilan protein to be conveyed to the skin at an appropriate dilution. The nature of the vehicle will depend upon the method chosen for administration of the composition. The vehicle can itself be inert or it can impart physiological or pharmaceutical benefits to the composition. Examples of pharmaceutically acceptable vehicles are water, squalene, liquid paraffin, a fatty acid, a monohydric alcohol, a polyhydric alcohol, or propylene glycol.

The vehicle for topical application of the composition of this invention can be based on water or at least one cosmetically acceptable vehicle other than water. It will be understood that nonaqueous cosmetically acceptable vehicles can also be combined with water to provide a composition suitable for topical application. Vehicles that can be employed in the composition of the invention include solids or liquids, such as emollients, solvents, humectants, thickeners, and powders. Examples of cosmetically acceptable vehicles are polyoxyethylene adduct of hardened castor oil, glycerol, dipropylene glycol, 1,3-butylene glycol, polyethylene glycol, cetylisooctanate, squalene, vaseline, propylparaben, water, liquid paraffin, cetostearyl alcohol, glyceryl monostearate, and ethylene oxide alkyl ether.

Modified maxadilan protein can be utilized in the methods and compositions of the present invention either alone, or in combination with other known treatment agents. For example, the modified maxadilan can be used in combination with one or more of the following agents: vasodilators, amino acids, skin-hyperactive agents, anti-inflammatories, refrigerants such as menthol, oils, higher fatty acids and higher alcohols, and polyhydric alcohols. Surfactants, perfumes, antioxidants, ultraviolet absorbers, pigments, ethanol, water, humectants, propellants, and thickeners, can optionally be employed in the methods and compositions of this invention to the extent that they do not detract from the effects of the invention.

Although the modified maxadilan protein of the invention can be employed at an extremely low level of the protein in the composition of the invention, generally, the modified maxadilan protein is employed in the amount of about $1\times10^{-5}$ to about 5% by weight per total weight of the composition, and preferably in an amount of about $1\times10^{-5}$ to about 3% by weight per total weight of the composition, in topical application.

The composition according to the invention can be either directly applied on the skin or applied by percutaneous injection. The dosage of the composition according to the invention varies depending on age, individual differences, symptoms, etc., but in the case of an adult, it is generally in the range of 500 fg to 500 mg, and preferably in the range of 100 pg to 100 mg, modified maxadilan protein per kg of body weight per day.

Vasodilation effects in an adult human can be achieved by administering the composition in an effective amount of about 100 fg to about 100 mg, preferably about 100 pg to about 100 mg, of modified maxadilan protein per kg of host body weight per day. In one embodiment, maxadilan can be applied to humans in an amount ranging from 100 fg to 100 mg, and preferably in the range from 100 pg to 100 mg, per square cm of surface area. Maxadilan is present in the topical composition in an amount of about $5.0\times10^{-10}$ to about $5.0\times10^{-1}$ percent by weight, preferably about $5.0\times10^{-8}$ to about $5.0\times10^{-3}$ percent by weight.

The exact regime used will depend on several factors such as the condition of the individual, but are readily determinable by the treating physician. Treatment should be continued at least until the desired effect is achieved.

(b) Composition for Subcutaneous Injection

In addition to topically applying the composition of this invention to the subject, the composition of the invention can also be administered to the subject by subcutaneous injection to induce, maintain or increase vasodilation. Modified maxadilan protein has an extremely good vasodilation effect so that it has an efficacy dose in animals of at least 1 pg per kg of host body weight per day by subcutaneous injection.

Native maxadilan proteins, as well as the modified maxadilan protein of this invention, are also useful in the methods and compositions described in U.S. patent application Ser. No. 017,061, filed Feb. 12, 1993, (Attorney Docket No. 05136.0002) the entire disclosure of which is relied upon and incorporated by reference herein.

EXAMPLE 1

Subcloning And Isolation Of Sand Fly Maxadilan cDNA

Maxadilan cDNA was obtained from the expression plasmid pGEX-3X-Max, which was provided by Lerner et al. This plasmid was cleaved with the restriction enzymes BamHI and EcoRI. 0.2 Kb fragments of DNA were isolated using phenol extraction from low temperature melted agarose. These fragments were subcloned into the subcloning vector M13mp10 and M13mp11. M13 mp10 and mp11 DNA were digested with the restriction enzymes BamHI and EcoRI and then BamHI and EcoRI-cleaved cDNA was inserted into these vectors using T4 DNA ligase.

Several different subclones were selected and the subcloned maxadilan cDNA was excised from the subcloning vectors by cleaving with the restriction enzymes BamHI and EcoRI or HindIII. Fragments having a size range of 0.2 kb were analyzed by restriction mapping and direct DNA sequencing. The DNA sequence of the fragments was determined by the Sequenase dideoxy chain termination method (United States Biochemical Corporation) using a DNA sequencer (Hitachi WS-10A).

EXAMPLE 2

Expression Of Maxadilan-GST Fusion Protein a. Construction Of Expression Vectors A plasmid, pUC19-Max (60K, 61A)-GK, having the maxadilan cDNA sequence as shown in FIG. 1, was used to generate the maxadilan fusion protein expression plasmid pGST-GSIL-Max(60K, 61A)-GK. A commercial expression vector which encodes the amino acid residues L-V-D-R SEQ ID NO: 23, pGEX-2T (Pharmacia) was cleaved with BamHI and EcoRI.

Plasmid pUC19-Max (60K, 61A)-GK was cleaved with BamHI and EcoRI to release the maxadilan cDNA sequence shown in FIG. 1. This cDNA sequence was inserted into BamHI and EcoRI-cleaved pGEX2T. Following this, the maxadilan cDNA-containing pGEX2T plasmid was cleaved with BamHI. The sticky ends were filled in with T4 DNA polymerase and then ligated. The final structure of vector pGST-GSIL-Max (60K, 61A)-GK is shown in FIG. 2. It contains GST coding sequence followed by DNA encoding L-V-P-R-G-S-I-L SEQ ID NO: 3, which is followed by maxadilan coding sequence. The sequence L-V-P-R-G-S-I-L SEQ ID NO: 3 encodes a thrombin cleavage site. The amino acid and DNA sequence of the GST-LVPR-GSIL-maxadilan fusion protein is shown in FIG. 3.

For comparison purposes, another expression plasmid, pGIL-Max(60K, 61A)-GK, was constructed using the method of Lerner et al., described on page 1063. This plasmid encodes a fusion protein comprising GST fused to the peptide E-G-R-G-I-L SEQ ID NO: 24, which is fused to maxadilan. The sequence E-G-R-G-I-L SEQ ID NO: 24 encodes a Factor Xa cleavage site. The amino acid and DNA sequence of the GST-EGRGIL-maxadilan fusion protein is shown in FIG. 4. When this fusion protein is cleaved with Factor Xa, the modified maxadilan produced has the N-terminal amino acid sequence G-I-L-C-D-A-T SEQ ID NO: 25. See J. Biol. Chem. 267, 1062–1066 (1992).

b. Transfection And Expression

The expression vector pGST-GSIL-Max(60K, 61A)-GK was transfected into *E. coli* HA101 using Mandell and Higa's method for transfection. Mandel, M., and Higa, A., 1970, Calcium dependent bacteriophage DNA Infection. J. Mol. Biol. 53, 154.

The transformed *E. coli* harboring the GST plasmid were grown in LB media at 37° C. for 3 hours. These cells were also induced with isopropyl-β-D-thio-galactopyranoside (IPTG) at a concentration of 2 millimoles for every $10^9$ cells. After five hours, the level of protein in the supernatant was 10% of the total cell protein. The bacteria were separated from the supernatant by centrifugation.

c. Fusion Protein Cleavage And Purification

The GSIL-maxadilan GST fusion protein in the supernatant was cleaved using 10 μg/ml thrombin (Mochida). Digestion proceeded for one hour at 37° C.

The GIL-maxadilan fusion protein was cleaved with Factor Xa at a concentration of 100 μg/ml for 5 hours at 37° C.

Following cleavage, GIL maxadilan protein and GSIL maxadilan protein were purified using RP-HPLC. A CAPCELL PAK C-8 SG 300 (Shiseido Co., Ltd.) column was used on a Shimadzu LC6A system from Shimazu Co. Ltd. Proteins were eluted using an acetonitrile gradient (0.1% TFA/water solution (pH 2.0) and 0.1% TFA/acetonitrile solution). The RP HPLC column was run for 20 minutes at a pressure of 50–100 kg-f/cm².

Figure 5B:
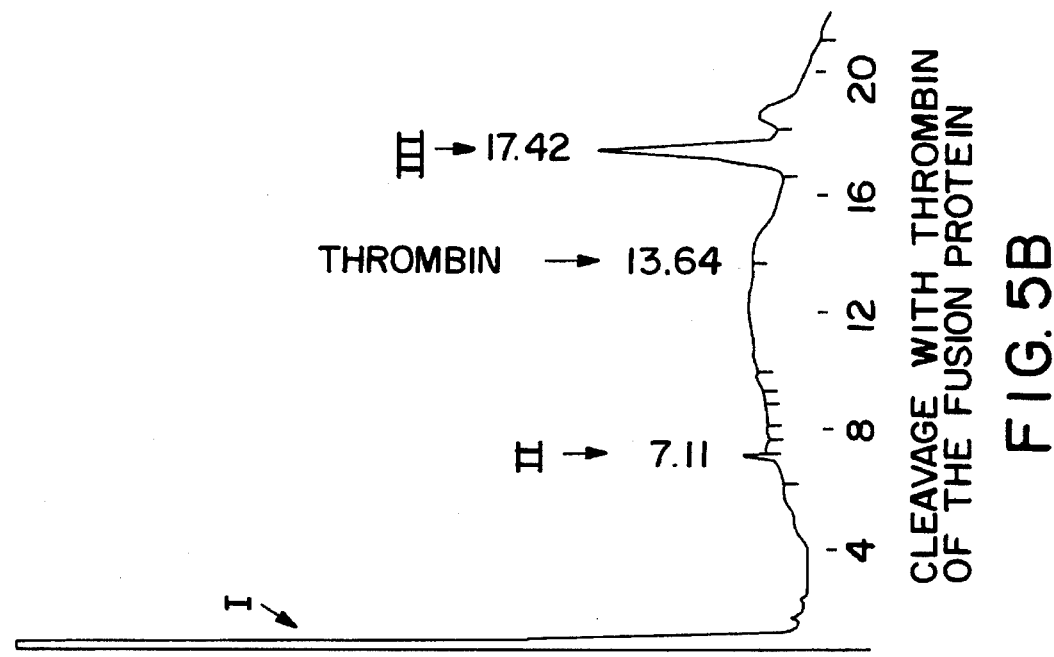
FIG. 5 (*a–b*) is the reverse phase HPLC elution profile for GSIL-maxadilan and GIL-maxadilan.
Figure 5A:
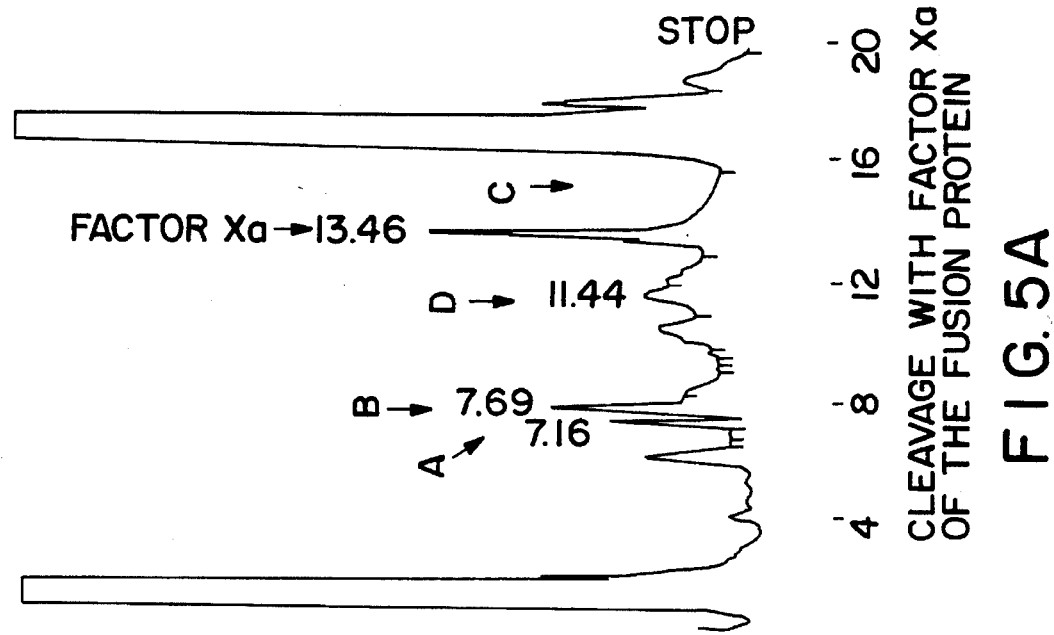
Figure 6:
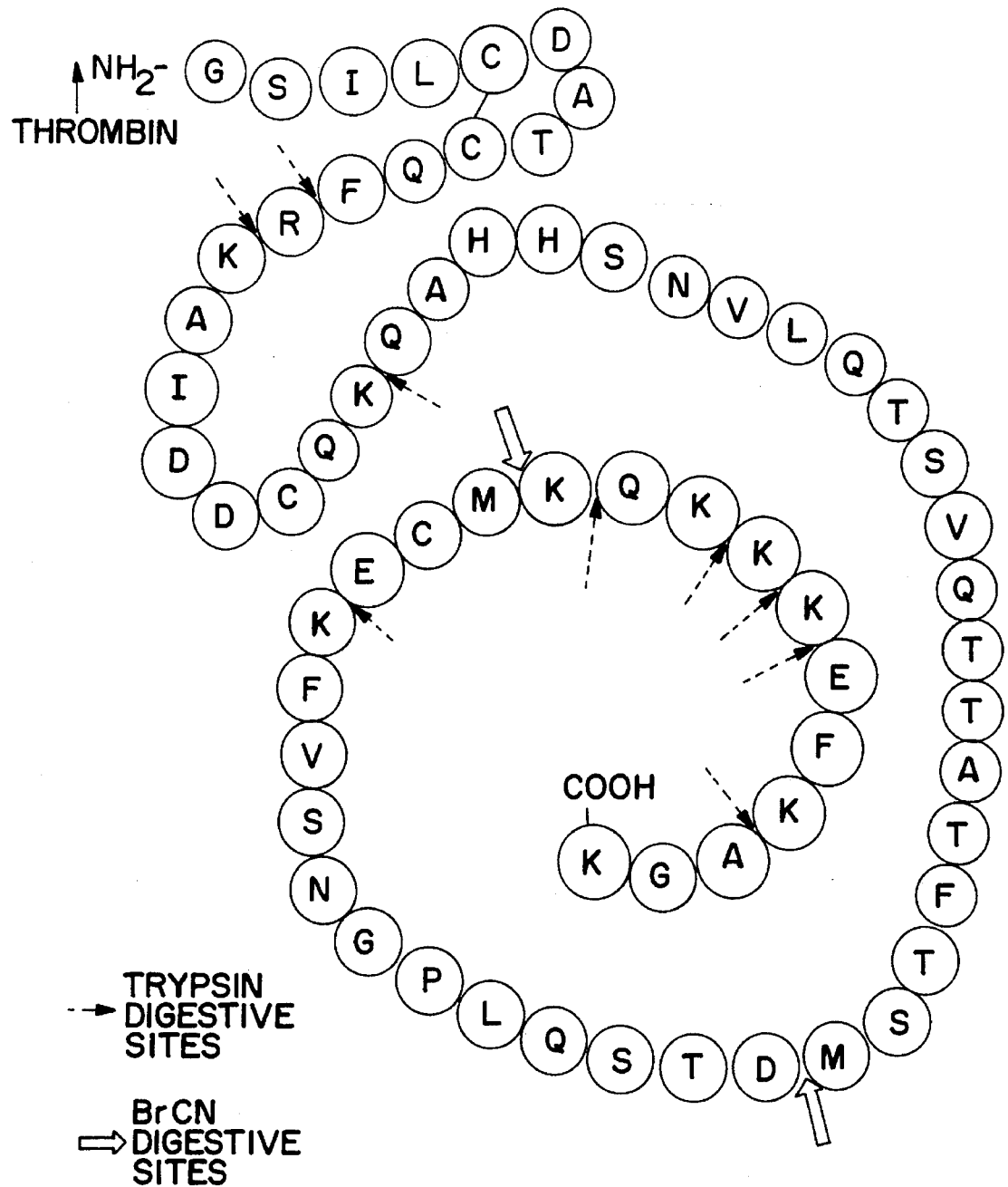
FIG. 6 depicts an amino acid sequence of a modified a maxadilan protein of the invention SEQ ID NO: 2.

The results of the RP HPLC purification of the GSIL and GIL maxadilan proteins are shown in FIG. 5. Material with a retention time of approximately 7.1 minutes was determined to be maxadilan using N-terminal peptide sequence analysis using an ABI 471A peptide sequencer. The protein migrating in this peak also had the size expected for a dimer of maxadilan which was determined from the SDS-PAGE data. The amino acid sequence of modified maxadilan protein is shown in FIG. 6. The amino acid and cDNA sequence of modified maxadilan protein is shown in FIG. 7.

The purity of the GSIL and GIL maxadilan proteins purified using RP HPLC were determined to be over 95% pure using RP-HPLC analysis data.

d. Comparison Of Protein Yield And Cleavage Enzyme Efficiency Of Fusion Proteins Cleaved With Thrombin Or Factor Xa A one-liter culture of *E. coli* transfected with the plasmid pGST-GSIL-Max(60K, 61A)-GK yielded 0.7 mg of GSIL-maxadilan protein following purification and cleavage of the fusion protein with thrombin. In contrast, a one-liter culture of *E. coli* transfected with pGIL yielded only 0.3 mg of GIL-maxadilan following purification and cleavage of the fusion protein with Factor Xa.

Table 1 summarizes the results of cleaving GST-maxadilan fusion proteins with either thrombin or Factor Xa:

TABLE 1

| Protein/Vector | GSIL-Maxadilan/ pGST-GSIL-Max (60K 61A)GK | GIL-Maxadilan/ pGST-GIL-Max (60K, 61A) |
| --- | --- | --- |
| Ratio (cleavage enzyme/fusion protein) | 1:15 (wt/wt) (thrombin) | 1:1 (wt/wt) (Factor Xa) |
| Concentration of thrombin or Factor Xa used | 0.06 mg/ml | 1 mg/ml |
| Amount of modified maxadilan produced from 1 liter culture | 0.7 mg | 0.3 mg |
| Cleavage | Complete | Incomplete |

Clearly, thrombin is more efficient at cleaving maxadilan fusion protein than Factor Xa. Thrombin is more efficient on a molar basis than Factor Xa. The molecular weights of thrombin and Factor Xa are 37 and 56 kDa, respectively.

EXAMPLE 3

Biological Activity Assays

The biological activities of GSIL-maxadilan, GIL-maxadilan, and native maxadilan were analyzed using a rabbit skin erythema assay according to the method of Lerner et al. at page 1063. Briefly, Japanese white rabbits were injected intradermally with GSIL-maxadilan, GIL-maxadilan or native maxadilan (Lerner et al.). Saline and calcitonin gene-related peptide (CGRP) were used as controls. CGRP is a vasodilator peptide. Lerner et al. at page 1065. The maxadilan proteins (all approximately 96% pure) were suspended in 0.9% saline solution at a concentration of $2 \times 10^{-5}$ μg/ml. 50 μl of protein or control solution was injected intradermally under the back skin of the rabbits. Photographs of the skin injected were taken at intervals between 15 minutes and 6 hours. The results of the erythema assay are shown in Table 2. Five separate determinations were made for each concentration of maxadilan or control substances tested.

TABLE 2

| Erythema activities on the rabbit skin | | | | |
| --- | --- | --- | --- | --- |
| Injection | (g) | 15 min | 1 hr | 6 hr |
| GSIL-MAX(60K, 61A)-GK | $10^9$ | + | + | + |
|  | $10^{-10}$ | + | + | + |
|  | $10^{-11}$ | + | + | + |
|  | $10^{-12}$ | + | + | + |
| Synthetic MAX (MAX-GK) | $10^{-9}$ | + | + | + |
|  | $10^{-10}$ | + | − | − |
|  | $10^{-11}$ | − | − | − |
|  | $10^{-12}$ | − | − | − |
| GIL-MAX(60K, 61A)-GK | $10^{-9}$ | + | + | − |
|  | $10^{-10}$ | + | + | − |

TABLE 2-continued

| Erythema activities on the rabbit skin | | | | |
|---|---|---|---|---|
| Injection | (g) | 15 min | 1 hr | 6 hr |
|  | $10^{-11}$ | − | − | − |
|  | $10^{-12}$ | − | − | − |
| CGRP | $10^{-9}$ | + | + | − |
|  | $10^{-10}$ | + | − | − |
|  | $10^{-11}$ | − | − | − |
|  | $10^{-12}$ | − | − | − |
| Saline |  | − | − | − |

The GSIL-maxadilan is more biologically active than either GIL-maxadilan or native maxadilan. Even injection of $10^{-11}$ or $10^{-12}$ g of GSIL-maxadilan stimulated erythema after 15 minutes, whereas GIL-maxadilan and native maxadilan were not active at these concentrations. After 6 hours, GSIL-maxadilan was still active even at a level of $10^{-12}$ g, whereas GIL- and native maxadilan were not active.

In summary, this invention makes it possible to more efficiently and less expensively produce large quantities of maxadilan. The recombinant modified maxadilan protein of the invention has high biological activity. In order to achieve these goals, maxadilan DNA has been cloned and the cloned DNA expressed using recombinant DNA methods to produce a fusion protein comprising a modified maxadilan protein. The fusion protein comprises GST fused at its C-terminus to the peptide L-V-P-R-G-S-I-L SEQ ID NO: 3, which is fused at its C-terminus to the N-terminus of maxadilan protein. The amino acid sequence L-V-P-R-G-S-I-L SEQ ID NO: 3 encodes a thrombin cleavage site and eliminates the Factor Xa cleavage site heretofore employed.

Cleavage of the GST fusion protein taught by Lerner et al. with Factor Xa yields a modified maxadilan protein with the N-terminal sequence G-I-L-C-D-A-T SEQ ID NO: 25, whereas the N-terminal sequence of native unmodified maxadilan is C-D-A-T SEQ ID NO: 22. When cleaved with thrombin, the fusion protein of the invention yields a modified maxadilan protein which has as its N-terminal sequence the amino acids G-S-I-L-C-D-A-T SEQ ID NO: 2.

Following are examples of compositions of this invention containing a modified maxadilan protein.

EXAMPLE 4

Oil-In-Water Emulsion

An emulsion is prepared from phase A, phase B, phase C, phase D, and phase E having the following compositions:

| Phase A | |
|---|---|
| Modified maxadilan protein | 1.0 |
| Polyoxyethylene (60 mol) adduct hardened castor oil | 2.0 |
| Glycerol | 10.0 |
| Dipropylene glycol | 10.0 |
| 1,3-Butylene glycol | 5.0 |
| Polyethylene glycol 1500 | 5.0 |
| Phase B | |
| Cetylisooctanate | 10.0 |
| Squalene | 5.0 |
| Vaseline | 2.0 |
| Propylparaben | 2.0 |
| Phase C | |
| Aqueous 1% solution of carboxyvinyl polymer | 30.0 |

| -continued | |
|---|---|
| Sodium hexametaphosphate | 0.03 |
| Deionized water | 8.35 |
| Phase D | |
| Deionized water | 4.5 |
| Phase E | |
| Potassium hydroxide | 0.12 |
| Deionized water | 5.0 |

Phase A and phase B are separately and thermally melted at 60° C. and then mixed with the homomixer to produce a gel. Phase D is gradually added thereto and dispersed by means of the homomixer.

Subsequently, the dispersed phase C is added thereto, and finally E phase is added followed by homomixer treatment to obtain an oil-in-water type emulsion.

EXAMPLE 5

Cream Composition

A cream is prepared from phase A and phase B having the following compositions:

| Phase A | |
|---|---|
| Modified maxadilan protein | 5.0 |
| Liquid paraffin | 5.0 |
| Cetostearyl alcohol | 5.5 |
| Glyceryl monostearate | 3.0 |
| EO (20 mol)-2-octyldodecyl ether | 3.0 |
| Propylparaben | 0.3 |
| Perfume | 0.1 |
| Phase B | |
| Glycerol | 8.0 |
| Dipropylene glycol | 20.0 |
| Polyethylene glycol 4000 | 5.0 |
| Sodium hexametaphosphate | 0.005 |
| Deionized water | 49.095 |

Phase A and phase B are each separately and thermally dissolved and were then mixed together. The mixture is emulsified by means of a homomixer to obtain a cream.

EXAMPLE 6

Gel Composition

A gel is prepared by combining five phases having the following compositions:

| Phase A | |
|---|---|
| Modified maxadilan protein | 3.0 |
| Polyoxyethylene (60 mol) adduct hardened castor oil | 2.0 |
| Glycerol | 10.0 |
| 1,3-Butylene Glycol | 5.0 |
| Polyethylene glycol 1500 | 5.0 |
| Phase B | |
| Cetylisooctanate | 10.0 |
| Vaseline | 8.0 |
| Propylparaben | 2.0 |
| Phase C | |
| Aqueous 1% solution of carboxyvinyl polymer | 30.0 |

-continued

| | |
|---|---|
| Sodium hexametaphosphate | 0.03 |
| Deionized water | 8.35 |
| Phase D | |
| Deionized water | 4.5 |
| Phase E | |
| Potassium hydroxide | 0.12 |
| Deionized water | 12.0 |

Phase A and phase B are separately and thermally melted at 60° C. and then mixed with homomixer to produce a gel. Phase D is gradually added thereto and dispersed by means of homomixer. Subsequently, the dispersed phase C is added thereto, and finally phase E is added followed by the homomixer treatment to obtain the gel composition.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A modified maxadilan protein, wherein the peptide G-S-I-L SEQ ID NO: 1 is fused to the N-terminus of native maxadilan protein.

2. Modified maxadilan protein according to claim 1, wherein the first eight amino acids at the N-terminus of said modified maxadilan protein are G-S-I-L-C-D-A-T SEQ ID NO. 2.

3. Modified maxadilan protein according to claim 1, having the amino acid sequence in FIG. 6 SEQ ID NO: 12.

4. Modified maxadilan protein according to claim 3, wherein the administration of $2 \times 10^{-7}$ g/l of said modified maxadilan protein stimulates skin erythema.

5. Modified maxadilan protein as claimed in claim 3, wherein said modified maxadilan protein is 10 times more active in stimulating skin erythema activity than native maxadilan protein.

6. A modified maxadilan fusion protein comprising the modified maxadilan protein as claimed in claim 1, wherein said modified maxadilan protein has an N-terminus and a peptide sequence containing Arg or Lys is fused proximate to the N-terminus of the modified maxadilan protein, wherein the peptide sequence contains a thrombin cleavage site, and wherein said modified maxadilan protein functions as a vasodilator following cleavage of said peptide sequence.

7. Modified maxadilan fusion protein as claimed in claim 6 comprising native maxadilan protein having the N-terminal sequence L-V-P-R-G-S-I-L SEQ ID NO. 3.

8. Modified maxadilan fusion protein as claimed in claim 7, wherein the bacterial protein glutathione S-transferase having a C-terminus is fused at the C-terminus to the N-terminus of the modified maxadilan protein.

9. Modified maxadilan fusion protein as claimed in claim 6 having the amino acid sequence in FIG. 3 SEQ ID NO: 9.

10. Modified maxadilan protein produced by a method comprising:.
   (a) culturing a transformed procaryotic or eucaryotic cell containing DNA encoding the protein according to claim 6 under growth conditions such that modified maxadilan fusion protein is produced; and
   (b) cleaving said fusion protein with thrombin to yield modified maxadilan protein.

11. A composition suitable for topical application to mammalian skin, wherein the composition comprises modified maxadilan protein as claimed in claim 1, in a vasodilation inducing, maintaining or increasing amount in a pharmaceutically acceptable vehicle.

12. The composition as claimed in claim 11, wherein said composition comprises modified maxadilan protein in a pharmaceutically acceptable vehicle selected from the group consisting of squalene, liquid paraffin, a lipid, a liposome, a fatty acid, a monohydric alcohol, a polyhydric alcohol, propylene glycol, or water.

13. The composition as claimed in claim 11, wherein said composition comprises modified maxadilan protein in a cosmetically acceptable vehicle selected from the group consisting of polyoxyethylene adduct of hardened castor oil, glycerol, dipropylene glycol, 1,3-butylene glycol, polyethylene glycol, cetylisooctanate, squalene, vaseline, propylparaben, water, liquid paraffin, cetostearyl alcohol, glyceryl monostearate, and ethylene oxide alkyl ether.

* * * * *

UNITED STATES PATENT AND TRADEMARK OFFICE
CERTIFICATE OF CORRECTION

PATENT NO. : 5,480,864
DATED : January 2, 1996
INVENTOR(S) : Masahiro TAJIMA et al.

It is certified that error appears in the above-indentified patent and that said Letters Patent is hereby corrected as shown below:

On the Title Page, item [73], after "Hospital" insert --Corp.--.

Claim 1, col. 35, line 56, change "SEQ ID NO:1" to --(SEQ ID NO:1)--.

Claim 2, col. 35, lines 61-62, change "SEQ ID NO:2" to --(SEQ ID NO:2)--.

Claim 7, col. 37, line 3, change "SEQ ID NO:3" to --(SEQ ID NO:3)--.

Signed and Sealed this

Nineteenth Day of March, 1996

Attest:

BRUCE LEHMAN

*Attesting Officer*  *Commissioner of Patents and Trademarks*

SEQUENCE LISTING ( 1 ) GENERAL INFORMATION:

( i i i ) NUMBER OF SEQUENCES: 25

( 2 ) INFORMATION FOR SEQ ID NO:1:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:1:

Gly  Ser  Ile  Leu
    1

( 2 ) INFORMATION FOR SEQ ID NO:2:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:2:

Gly  Ser  Ile  Leu  Cys  Asp  Ala  Thr
    1                        5

( 2 ) INFORMATION FOR SEQ ID NO:3:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:3:

Leu  Val  Pro  Arg  Gly  Ser  Ile  Leu
    1                        5

( 2 ) INFORMATION FOR SEQ ID NO:4:

( i ) SEQUENCE CHARACTERISTICS:
        ( A ) LENGTH: 207 base pairs
        ( B ) TYPE: nucleic acid
        ( C ) STRANDEDNESS: single (D) TOPOLOGY: linear (ii) MOLECULE TYPE: DNA (genomic)

(xi) SEQUENCE DESCRIPTION: SEQ ID NO:4:

| | | | | | |
|---|---|---|---|---|---|
| GGATCCTGCT | GTGTGATGCA | ACATGCCAAT | TTCGCAAGGC | CATAGATGAC | TGCCAGAAGC | 60
| AGGCGCATCA | TAGCAATGTT | TTGCAGACTT | CTGTACAAAC | AACTGCAACA | TTCACATCAA | 120
| TGGATACCTC | CCAACTACCT | GGAAATAGTG | TCTTCAAAGA | ATGTATGAAG | CAGAAGAAAA | 180
| AGGAATTTAA | GGCAGGAAAG | TGAATTC | | | | 207

(2) INFORMATION FOR SEQ ID NO:5:

(i) SEQUENCE CHARACTERISTICS:
        (A) LENGTH: 65 amino acids
        (B) TYPE: amino acid
        (D) TOPOLOGY: linear (ii) MOLECULE TYPE: peptide (xi) SEQUENCE DESCRIPTION: SEQ ID NO:5:

```
Ile Leu Cys Asp Ala Thr Cys Gln Phe Arg Lys Ala Ile Asp Asp Cys
 1               5                  10                 15
Gln Lys Gln Ala His His Ser Asn Val Leu Gln Thr Ser Val Gln Thr
            20                  25                  30
Thr Ala Thr Phe Thr Ser Met Asp Thr Ser Gln Leu Pro Gly Asn Ser
         35                  40                  45
Val Phe Lys Glu Cys Met Lys Gln Lys Lys Lys Glu Phe Lys Ala Gly
     50                  55                  60
Lys
65
```

(2) INFORMATION FOR SEQ ID NO:6:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

CTGGTTCCGC GCGGATCGAT CCTG                            24

(2) INFORMATION FOR SEQ ID NO:7:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

TTAAAGTGAA TTCATCGT                                   18

(2) INFORMATION FOR SEQ ID NO:8:

(i) SEQUENCE CHARACTERISTICS:
        (A) LENGTH: 897 base pairs
        (B) TYPE: nucleic acid
        (C) STRANDEDNESS: single -continued ( D ) TOPOLOGY: linear ( i i ) MOLECULE TYPE: DNA (genomic)

( x i ) SEQUENCE DESCRIPTION: SEQ ID NO:8:

```
ATGTCCCTA  TACTAGGTTA  TTGGAAAATT  AAGGGCGTTG  TGCAACCCAC  TCGACTTCTT    60
TTGGAATATC  TTGAAGAAAA  ATATGAAGAG  CATTTGTATG  AGCGCGATGA  AGGTGATAAA   120
TGGCTAAACA  AAAAGTTTGA  ATTGGGTTTG  GAGTTTCCCA  ATCTTCCTTA  TTATATTGAT   180
GGTGATGTTA  AATTAACACA  GTCTATGGCC  ATCATAGGTT  ATATAGCTGA  CAAGCACAAC   240
ATGTTGGGTG  GTTGTCCAAA  AGAGCGTGCA  GAGATTTCAA  TGCTTGAAGG  AGCGGTTTTG   300
GATATTAGAT  ACGGTGTTTC  GAGAATTGCA  TATAGTAAAG  ACTTTGAAAC  TCTCAAAGTT   360
GATTTTCTTA  GCAAGCTACC  TCAAATGCTG  AAAATGTTCG  AAGATCGTTT  ATGTCATAAA   420
ACATATTTAA  ATGGTGATCA  TGTAACCCAT  CCTGACTTCA  TGTTGTATGA  CGCTCTTGAT   480
GTTGTTTTAT  ACATGGACCC  AATGTGCCTG  GATGCGTTCC  CAAAATTAGT  TTGTTTTAAA   540
AAACGTATTG  AAGCTATCCC  ACAAATTGAT  AAGTACTTGA  ATCCAGCAA   GTATATACCA   600
TGGCCTTTGC  AGGGCTGGCA  AGCCACGTTT  GGTGGTGGCG  ACCATCCTCC  AAAATCGGAT   660
CTGGTTCCGC  GCGGATCGAT  CCTGTGTGAT  GCAACATGCC  AATTTCGCAA  GGCCATAGAT   720
GACTGCCAGA  AGCAGGCGCA  TCATAGCAAT  GTTTTGCAGA  CTTCTGTACA  ACAACTGCA    780
ACATTCACAT  CAATGGATAC  CTCCCAACTA  CCTGGAAATA  GTGTCTTCAA  AGAATGTATG   840
AAGCAGAAGA  AAAAGGAATT  TAAGGCAGGA  AAGTGAATTC  ATCCTGACTG  ACTCACG      897
```

( 2 ) INFORMATION FOR SEQ ID NO:9:

( i ) SEQUENCE CHARACTERISTICS:
( A ) LENGTH: 291 amino acids
( B ) TYPE: amino acid
( D ) TOPOLOGY: linear ( i i ) MOLECULE TYPE: peptide ( x i ) SEQUENCE DESCRIPTION: SEQ ID NO:9:

```
Met  Ser  Pro  Ile  Leu  Gly  Tyr  Trp  Lys  Ile  Lys  Gly  Leu  Val  Gln  Pro
 1              5                        10                       15

Thr  Arg  Leu  Leu  Leu  Glu  Tyr  Leu  Glu  Glu  Lys  Tyr  Glu  Glu  His  Leu
               20                       25                       30

Tyr  Glu  Arg  Asp  Glu  Gly  Asp  Lys  Trp  Leu  Asn  Lys  Lys  Phe  Glu  Leu
          35                       40                       45

Gly  Leu  Glu  Phe  Pro  Asn  Leu  Pro  Tyr  Tyr  Ile  Asp  Gly  Asp  Val  Lys
     50                       55                       60

Leu  Thr  Gln  Ser  Met  Ala  Ile  Ile  Arg  Tyr  Ile  Ala  Asp  Lys  His  Asn
65                       70                       75                       80

Met  Leu  Gly  Gly  Cys  Pro  Lys  Glu  Arg  Ala  Glu  Ile  Ser  Met  Leu  Glu
                    85                       90                       95

Gly  Ala  Val  Leu  Asp  Ile  Arg  Tyr  Gly  Val  Ser  Arg  Ile  Ala  Tyr  Ser
               100                      105                      110

Lys  Asp  Phe  Glu  Thr  Leu  Lys  Val  Asp  Phe  Leu  Ser  Lys  Leu  Pro  Arg
          115                      120                      125

Met  Leu  Lys  Met  Phe  Glu  Asp  Arg  Leu  Cys  His  Lys  Thr  Tyr  Leu  Asn
     130                      135                      140

Gly  Asp  His  Val  Thr  His  Pro  Asp  Phe  Met  Leu  Tyr  Asp  Ala  Leu  Asp
145                      150                      155                      160

Val  Val  Leu  Tyr  Met  Asp  Pro  Met  Cys  Leu  Asp  Ala  Phe  Pro  Lys  Leu
```

|  |  |  | 165 |  |  |  |  | 170 |  |  |  |  | 175 |  |
|---|---|---|---|---|---|---|---|---|---|---|---|---|---|---|
| Val | Cys | Phe | Lys<br>180 | Lys | Arg | Ile | Glu | Ala<br>185 | Ile | Pro | Gln | Ile | Asp<br>190 | Lys | Tyr |
| Leu | Lys | Ser | Ser<br>195 | Lys | Tyr | Ile | Ala | Trp<br>200 | Pro | Leu | Gln | Gly<br>205 | Trp | Gln | Ala |
| Thr | Phe | Gly<br>210 | Gly | Gly | Asp | His<br>215 | Pro | Pro | Lys | Ser | Asp<br>220 | Leu | Val | Pro | Arg |
| Gly<br>225 | Ser | Ile | Leu | Cys | Asp<br>230 | Ala | Thr | Cys | Gln | Phe<br>235 | Arg | Lys | Ala | Ile | Asp<br>240 |
| Asp | Cys | Gln | Lys | Gln<br>245 | Ala | His | His | Ser | Asn<br>250 | Val | Leu | Gln | Thr | Ser<br>255 | Val |
| Gln | Thr | Thr | Ala<br>260 | Thr | Phe | Thr | Ser | Met<br>265 | Asp | Thr | Ser | Gln | Leu<br>270 | Pro | Gly |
| Asn | Ser | Val<br>275 | Phe | Lys | Glu | Cys | Met<br>280 | Lys | Gln | Lys | Lys | Lys<br>285 | Glu | Phe | Lys |
| Ala | Gly | Lys<br>290 |  |  |  |  |  |  |  |  |  |  |  |  |  |

( 2 ) INFORMATION FOR SEQ ID NO:10:

( i ) SEQUENCE CHARACTERISTICS:
        ( A ) LENGTH: 897 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:10:

| ATGTCCCTA | TACTAGGTTA | TTGGAAAATT | AAGGGCGTTG | TGCAACCCAC | TCGACTTCTT | 60 |
|---|---|---|---|---|---|---|
| TTGGAATATC | TTGAAGAAAA | ATATGAAGAG | CATTTGTATG | AGCGCGATGA | AGGTGATAAA | 120 |
| TGGCTAAACA | AAAAGTTTGA | ATTGGGTTTG | GAGTTTCCCA | ATCTTCCTTA | TTATATTGAT | 180 |
| GGTGATGTTA | AATTAACACA | GTCTATGGCC | ATCATAGGTT | ATATAGCTGA | CAAGCACAAC | 240 |
| ATGTTGGGTG | GTTGTCCAAA | AGAGCGTGCA | GAGATTTCAA | TGCTTCAAGC | ACCCCTTTTC | 300 |
| GATATTAGAT | ACGGTGTTTC | GAGAATTGCA | TATAGTAAAG | ACTTTGAAAC | TCTCAAAGTT | 360 |
| GATTTCTTA | GCAAGCTACC | TGAAATGCTG | AAAATGTTCG | AAGATCGTTT | ATGTCATAAA | 420 |
| ACATATTTAA | ATGGTGATCA | TGTAACCCAT | CCTGACTTCA | TGTTGTATGA | CGCTCTTGAT | 480 |
| GTTGTTTTAT | ACATGGACCC | AATGTGCCTG | GATGCGTTCC | CAAAATTAGT | TTGTTTTAAA | 540 |
| AAACGTATTG | AAGCTATCCC | ACAAATTGAT | AAGTACTTGA | ATCCAGCAA | GTATATAGCA | 600 |
| TGGCCTTTGC | AGGGCTGGCA | AGCCACGTTT | GGTGGTGGCG | ACCATCCTCC | AAAATCGGAT | 660 |
| CTGATCGAAG | GTCGTGGGAT | CCTGTGTGAT | GCAACATGCC | AATTTCGCAA | GGCCATAGAT | 720 |
| GACTGCCAGA | AGCAGGCGCA | TCATAGCAAT | GTTTTGCAGA | CTTCTGTACA | ACAACTGCA | 780 |
| ACATTCACAT | CAATGGATAC | CTCCCAACTA | CCTGGAAATA | GTGTCTTCAA | AGAATGTATG | 840 |
| AAGCAGAAGA | AAAAGGAATT | TAAGGCAGGA | AAGTGAATTC | ATCGTGACTG | ACTCACG | 897 |

( 2 ) INFORMATION FOR SEQ ID NO:11:

( i ) SEQUENCE CHARACTERISTICS:
        ( A ) LENGTH: 291 amino acids
        ( B ) TYPE: amino acid
        ( D ) TOPOLOGY: linear ( i i ) MOLECULE TYPE: peptide

5,480,864

27

-continued ( x i ) SEQUENCE DESCRIPTION: SEQ ID NO:11:

| Met | Ser | Pro | Ile | Leu | Gly | Tyr | Trp | Lys | Ile | Lys | Gly | Leu | Val | Gln | Pro |
|---|---|---|---|---|---|---|---|---|---|---|---|---|---|---|---|
| 1 | | | | 5 | | | | | 10 | | | | | 15 | |
| Thr | Arg | Leu | Leu | Leu | Glu | Tyr | Leu | Glu | Glu | Lys | Tyr | Glu | Glu | His | Leu |
| | | | 20 | | | | | 25 | | | | | 30 | | |
| Tyr | Glu | Arg | Asp | Glu | Gly | Asp | Lys | Trp | Leu | Asn | Lys | Lys | Phe | Glu | Leu |
| | | 35 | | | | | 40 | | | | | 45 | | | |
| Gly | Leu | Glu | Phe | Pro | Asn | Leu | Pro | Tyr | Tyr | Ile | Asp | Gly | Asp | Val | Lys |
| | 50 | | | | | 55 | | | | | 60 | | | | |
| Leu | Thr | Gln | Ser | Met | Ala | Ile | Ile | Arg | Tyr | Ile | Ala | Asp | Lys | His | Asn |
| 65 | | | | | 70 | | | | | 75 | | | | | 80 |
| Met | Leu | Gly | Gly | Cys | Pro | Lys | Glu | Arg | Ala | Glu | Ile | Ser | Met | Leu | Glu |
| | | | | 85 | | | | | 90 | | | | | 95 | |
| Gly | Ala | Val | Leu | Asp | Ile | Arg | Tyr | Gly | Val | Ser | Arg | Ile | Ala | Tyr | Ser |
| | | | 100 | | | | | 105 | | | | | 110 | | |
| Lys | Asp | Phe | Glu | Thr | Leu | Lys | Val | Asp | Phe | Leu | Ser | Lys | Leu | Pro | Glu |
| | | 115 | | | | | 120 | | | | | 125 | | | |
| Met | Leu | Lys | Met | Phe | Glu | Asp | Arg | Leu | Cys | His | Lys | Thr | Tyr | Leu | Asn |
| | 130 | | | | | 135 | | | | | 140 | | | | |
| Gly | Asp | His | Val | Thr | His | Pro | Asp | Phe | Met | Leu | Tyr | Asp | Ala | Leu | Asp |
| 145 | | | | | 150 | | | | | 155 | | | | | 160 |
| Val | Val | Leu | Tyr | Met | Asp | Pro | Met | Cys | Leu | Asp | Ala | Phe | Pro | Lys | Leu |
| | | | | 165 | | | | | 170 | | | | | 175 | |
| Val | Cys | Phe | Lys | Lys | Arg | Ile | Glu | Ala | Ile | Pro | Gln | Ile | Asp | Lys | Tyr |
| | | | 180 | | | | | 185 | | | | | 190 | | |
| Leu | Lys | Ser | Ser | Lys | Tyr | Ile | Ala | Trp | Pro | Leu | Gln | Gly | Trp | Gln | Ala |
| | | | 195 | | | | | 200 | | | | | 205 | | |
| Thr | Phe | Gly | Gly | Gly | Asp | His | Pro | Pro | Lys | Ser | Asp | Leu | Ile | Glu | Gly |
| | 210 | | | | | 215 | | | | | 220 | | | | |
| Arg | Gly | Ile | Leu | Cys | Asp | Ala | Thr | Cys | Gln | Phe | Arg | Lys | Ala | Ile | Asp |
| 225 | | | | | 230 | | | | | 235 | | | | | 240 |
| Asp | Cys | Gln | Lys | Gln | Ala | His | His | Ser | Asn | Val | Leu | Gln | Thr | Ser | Val |
| | | | | 245 | | | | | 250 | | | | | 255 | |
| Gln | Thr | Thr | Ala | Thr | Phe | Thr | Ser | Met | Asp | Thr | Ser | Gln | Leu | Pro | Gly |
| | | | 260 | | | | | 265 | | | | | 270 | | |
| Asn | Ser | Val | Phe | Lys | Glu | Cys | Met | Lys | Gln | Lys | Lys | Lys | Glu | Phe | Lys |
| | | 275 | | | | | 280 | | | | | 285 | | | |
| Ala | Gly | Lys |
| | | 290 |

( 2 ) INFORMATION FOR SEQ ID NO:12:

( i ) SEQUENCE CHARACTERISTICS:
        ( A ) LENGTH: 67 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:12:

| Gly | Ser | Ile | Leu | Cys | Asp | Ala | Thr | Cys | Gln | Phe | Arg | Lys | Ala | Ile | Asp |
|---|---|---|---|---|---|---|---|---|---|---|---|---|---|---|---|
| 1 | | | | 5 | | | | | 10 | | | | | 15 | |
| Asp | Cys | Gln | Lys | Gln | Ala | His | His | Ser | Asn | Val | Leu | Gln | Thr | Ser | Val |
| | | | 20 | | | | | 25 | | | | | 30 | | |
| Gln | Thr | Thr | Ala | Thr | Phe | Thr | Ser | Met | Asp | Thr | Ser | Gln | Leu | Pro | Gly |
| | | | 35 | | | | | 40 | | | | | 45 | | |

Asn  Ser  Val  Phe  Lys  Glu  Cys  Met  Lys  Gln  Lys  Lys  Lys  Glu  Phe  Lys
                         50                       55                      60

Ala  Gly  Lys
                    65

( 2 ) INFORMATION FOR SEQ ID NO:13:

( i ) SEQUENCE CHARACTERISTICS:
                ( A ) LENGTH: 207 base pairs
                ( B ) TYPE: nucleic acid
                ( C ) STRANDEDNESS: single
                ( D ) TOPOLOGY: linear ( i i ) MOLECULE TYPE: DNA (genomic)

( x i ) SEQUENCE DESCRIPTION: SEQ ID NO:13:

| GGATCGATCC | TGCTGTGTGA | TGCAACATGC | CAATTTCGCA | AGGCCATAGA | TGACTGCCAG | 60 |
| AAGCAGGCGC | ATCATAGCAA | TGTTTTGCAG | ACTTCTGTAC | AAACAACTGC | AACATTCACA | 120 |
| TCAATGGATA | CCTCCCAACT | ACCTGGAAAT | AGTGTCTTCA | AAGAATGTAT | GAAGCAGAAG | 180 |
| AAAAAGGAAT | TTAAGGCAGG | AAAGTAA | | | | 207 |

( 2 ) INFORMATION FOR SEQ ID NO:14:

( i ) SEQUENCE CHARACTERISTICS:
                ( A ) LENGTH: 313 base pairs
                ( B ) TYPE: nucleic acid
                ( C ) STRANDEDNESS: single
                ( D ) TOPOLOGY: linear ( i i ) MOLECULE TYPE: DNA (genomic)

( x i ) SEQUENCE DESCRIPTION: SEQ ID NO:14:

| TGTGATGCAA | CATGCCAATT | TCGCAAGKCC | ATAGATGACT | GCCAGAAGCA | GGCGCATCAT | 60 |
| AGCAATGTTT | TGCAGACTTC | TGTACAAACA | ACTGCAACAT | TCACATCAAT | GGATACCTCC | 120 |
| CAACTACCTG | GAAATAGTGT | CTTCAAAGAA | TGTATGAAGC | AGAAGAAAAA | GGAATTTAAG | 180 |
| GCAGGAAAGT | AAAATGATTG | AAGAAAATTG | TAGCCGAGGA | GAGAAAGAAA | GAAAGTCCCA | 240 |
| TACCATATTT | TGTTTGTTAA | TTGTAACGAA | TTTTCCGAAA | AAATAAAATA | TTATGCACTC | 300 |
| AATTTAAAAA | AAA | | | | | 313 |

( 2 ) INFORMATION FOR SEQ ID NO:15:

( i ) SEQUENCE CHARACTERISTICS:
                ( A ) LENGTH: 63 amino acids
                ( B ) TYPE: amino acid
                ( D ) TOPOLOGY: linear ( i i ) MOLECULE TYPE: DNA (genomic)

( x i ) SEQUENCE DESCRIPTION: SEQ ID NO:15:

Cys  Asp  Ala  Thr  Cys  Gln  Phe  Arg  Lys  Ala  Ile  Asp  Asp  Cys  Gln  Lys
        1                   5                        10                      15

Gln  Ala  His  His  Ser  Asn  Val  Leu  Gln  Thr  Ser  Val  Gln  Thr  Thr  Ala
                       20                       25                      30

Thr  Phe  Thr  Ser  Met  Asp  Thr  Ser  Gln  Leu  Pro  Gly  Asn  Ser  Val  Phe
                  35                       40                      45

Lys  Glu  Cys  Met  Lys  Gln  Lys  Lys  Lys  Glu  Phe  Lys  Ala  Gly  Lys
             50                       55                      60

( 2 ) INFORMATION FOR SEQ ID NO:16:

( i ) SEQUENCE CHARACTERISTICS:
    ( A ) LENGTH: 243 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:16:

| | | | | | | |
|---|---|---|---|---|---|---|
| ATGAAATATT | CTTTAAATAA | TCTCCATTTT | CTTGTAGACG | TTGCTGAGGG | CTGTGATGCA | 60 |
| ACATGTCAAT | TTCGCAAGGC | CATAGAAGAC | TGCAGGAAGA | AGGCGCATCA | TAGCGATGTT | 120 |
| TTGCAGACTT | CTGTACAAAC | AACTGCAACA | TTTACATCAA | TGGATACCTC | CCAACTACCT | 180 |
| GGAAGTGGTG | TTTTCAAAGA | ATGCATGAAG | GAGAAAGCTA | AGGAATTTAA | GGCAGGAAAG | 240 |
| TAG | | | | | | 243 |

( 2 ) INFORMATION FOR SEQ ID NO:17:

( i ) SEQUENCE CHARACTERISTICS:
    ( A ) LENGTH: 80 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:17:

```
Met Lys Tyr Ser Leu Asn Asn Leu His Phe Leu Val Asp Val Ala Glu
 1               5                  10                  15

Gly Cys Asp Ala Thr Cys Gln Phe Arg Lys Ala Ile Glu Asp Cys Arg
             20                  25                  30

Lys Lys Ala His His Ser Asp Val Leu Gln Thr Ser Val Gln Thr Thr
             35                  40                  45

Ala Thr Phe Thr Ser Met Asp Thr Ser Gln Leu Pro Gly Ser Gly Val
             50                  55                  60

Phe Lys Glu Cys Met Lys Gln Lys Ala Lys Glu Phe Lys Ala Gly Lys
65                   70                  75                  80
```

( 2 ) INFORMATION FOR SEQ ID NO:18:

( i ) SEQUENCE CHARACTERISTICS:
    ( A ) LENGTH: 325 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:18:

| | | | | | | |
|---|---|---|---|---|---|---|
| GCYACCGAYC | AGTTCCGYAA | GGCYATYGAY | GACTGCCAGA | AGCAGGCGCA | TCATAGCAAT | 60 |
| GTTTTGCAGA | CTTCTGTACA | AACAACTGCA | ACATTCACAT | CAATGGATAC | CTCCCAACTA | 120 |
| CCTGGAAATA | GTGTCTTCAA | AGAATGTATG | AAGCAGAAGA | AAAAGGAATT | TAGTTCAGGA | 180 |
| AAGTAAAAGA | TTGAAGAAAA | TTGTAGCCGA | GGAGAGAAAG | AAAGAAAGTC | CCATACCATA | 240 |
| TTTTGTTTGT | TAATTGTAAC | GAATTTTCCG | AAAAAATAAA | ATATTATGCA | CTCAATTTAA | 300 |
| AAAAAAAAAA | AAAAAGGGGC | CTCCC | | | | 325 |

( 2 ) INFORMATION FOR SEQ ID NO:19:

( i ) SEQUENCE CHARACTERISTICS:
    ( A ) LENGTH: 50 amino acids
    ( B ) TYPE: amino acid (D) TOPOLOGY: linear (ii) MOLECULE TYPE: peptide (xi) SEQUENCE DESCRIPTION: SEQ ID NO:19:

| Cys | Gln | Lys | Gln | Ala | His | His | Ser | Asn | Val | Leu | Gln | Thr | Ser | Val | Gln |
|---|---|---|---|---|---|---|---|---|---|---|---|---|---|---|---|
| 1 | | | | 5 | | | | | 10 | | | | | 15 | |

| Thr | Thr | Ala | Thr | Phe | Thr | Ser | Met | Asp | Thr | Ser | Gln | Leu | Pro | Gly | Asn |
|---|---|---|---|---|---|---|---|---|---|---|---|---|---|---|---|
| | | | 20 | | | | | 25 | | | | | 30 | | |

| Ser | Val | Phe | Lys | Glu | Cys | Met | Lys | Gln | Lys | Lys | Lys | Glu | Phe | Ser | Ser |
|---|---|---|---|---|---|---|---|---|---|---|---|---|---|---|---|
| | | | 35 | | | | | 40 | | | | | 45 | | |

Gly Lys
50

(2) INFORMATION FOR SEQ ID NO:20:

(i) SEQUENCE CHARACTERISTICS:
(A) LENGTH: 573 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:20:

| AATCAATTGC | TAAAAAAAAA | TTACAAATAG | AACTACTACA | GATGTTCTGA | ATTTTTTCTT | 60 |
| GATATTCTTT | CTCAATTGGA | TGTATAAAAG | AGGCTATTTT | GTGCTGATTT | TGTTAGTCAG | 120 |
| TATTCTGATA | AACTACAAAA | ATGAAGCAAA | TCCTTTTAAT | CTCTTTGGTG | GTGGTTCTTG | 180 |
| CCGTGTTTGC | CTTCAGTAAG | TTCTTCCTTT | AGGCCTTTCC | TTCTCAAAAC | TTAAAGTAAT | 240 |
| TTAATGAAAT | ATTCTTTAAA | TAATCTCCAT | TTTCTTGTAG | ACGTTGCTGA | GGGCTGTGAT | 300 |
| GCAACATGCC | AATTTCGCAA | GGCCATAGAT | GACTGCCAGA | AGCAGGCGCA | TCATAGCAAT | 360 |
| GTTTTGCAGA | CTTCTGTACA | AACAACTGCA | ACATTCACAT | CAATGGATAC | CTCCCAACTA | 420 |
| CCTGGAAATA | GTGTCTTCAA | AGAATGTATG | AAGCAGAAGA | AAAAGGAATT | TAGTTCAGGA | 480 |
| AAGTAAAAGA | TTGAAGAAAA | TTGTAGCCGA | GGAGAGAAAG | AAAGAAAGTC | CCATACCATA | 540 |
| TTTTGTTTGT | TAATTGTAAC | GAATTTTCCG | AAA | | | 573 |

(2) INFORMATION FOR SEQ ID NO:21:

(i) SEQUENCE CHARACTERISTICS:
(A) LENGTH: 86 amino acids
(B) TYPE: amino acid
(D) TOPOLOGY: linear (ii) MOLECULE TYPE: peptide (xi) SEQUENCE DESCRIPTION: SEQ ID NO:21:

| Met | Lys | Gln | Ile | Leu | Leu | Ile | Ser | Leu | Val | Val | Leu | Ala | Val | Phe |
|---|---|---|---|---|---|---|---|---|---|---|---|---|---|---|
| 1 | | | | 5 | | | | | 10 | | | | | 15 |

| Ala | Phe | Asn | Val | Ala | Glu | Gly | Cys | Asp | Ala | Thr | Cys | Gln | Phe | Arg | Lys |
|---|---|---|---|---|---|---|---|---|---|---|---|---|---|---|---|
| | | | 20 | | | | | 25 | | | | | 30 | | |

| Ala | Ile | Asp | Asp | Cys | Gln | Lys | Gln | Ala | His | His | Ser | Asn | Val | Leu | Gln |
|---|---|---|---|---|---|---|---|---|---|---|---|---|---|---|---|
| | | | 35 | | | | | 40 | | | | | 45 | | |

| Thr | Ser | Val | Gln | Thr | Thr | Ala | Thr | Phe | Thr | Ser | Met | Asp | Thr | Ser | Gln |
|---|---|---|---|---|---|---|---|---|---|---|---|---|---|---|---|
| | | 50 | | | | | 55 | | | | | 60 | | | |

| Leu | Pro | Gly | Asn | Ser | Val | Phe | Lys | Glu | Cys | Met | Lys | Gln | Lys | Lys | Lys |
|---|---|---|---|---|---|---|---|---|---|---|---|---|---|---|---|
| 65 | | | | | 70 | | | | | 75 | | | | | 80 |

Glu Phe Ser Ser Gly Lys ( 2 ) INFORMATION FOR SEQ ID NO:22:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:22:

Cys Asp Ala Thr
    1

( 2 ) INFORMATION FOR SEQ ID NO:23:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:23:

Leu Val Pro Arg
    1

( 2 ) INFORMATION FOR SEQ ID NO:24:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:24:

Glu Gly Arg Gly Ile Leu
    1                   5

( 2 ) INFORMATION FOR SEQ ID NO:25:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:25:

Gly Ile Leu Cys Asp Ala Thr
    1               5